(12) United States Patent
Bach et al.

(10) Patent No.: US 6,413,780 B1
(45) Date of Patent: Jul. 2, 2002

(54) STRUCTURE AND METHOD FOR PERFORMING A DETERMINATION OF AN ITEM OF INTEREST IN A SAMPLE

(75) Inventors: Mark C. Bach, Gurnee; Daniel Bay, Antioch; Michael K. Carter, Lake Villa; John M. Clemens, Wadsworth; Daniel G. Dahlke, Libertyville, all of IL (US); Charles M. Galitz, Kenosha, WI (US); Robert C. Gray, Gurnee, IL (US); Folim Halaka, North Chicago, IL (US); Steve Herchenbach, Antioch, IL (US); Ronald E. Kukla, Wheeling, IL (US); Curtis J. Pepe, McHenry, IL (US); Mark Pierce, Wauconda, IL (US); Scott G. Safar, Pleasant Prairie, WI (US); Julius Toth, Mundelein; Gary Zuck, Prospect Heights, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/415,796

(22) Filed: Oct. 11, 1999

Related U.S. Application Data

(60) Provisional application No. 60/104,191, filed on Oct. 14, 1998.

(51) Int. Cl.⁷ .............................................. G01N 35/02
(52) U.S. Cl. .............................. 436/48; 436/43; 436/47; 436/49; 436/164; 436/172; 422/63; 422/64; 422/65; 422/68.1; 422/82.05; 435/287.1; 198/347.3; 198/347.4
(58) Field of Search .............................. 422/63, 64, 65, 422/68.1, 81, 82.05, 82.08, 100; 435/287.1, 287.2, 287.3, 288.7; 436/43, 47, 48, 49, 164, 172; 198/347.3–347.4, 465.2

(56) References Cited

U.S. PATENT DOCUMENTS

| | | | | |
|---|---|---|---|---|
| 3,883,305 A | * | 5/1975 | Hoskins et al. | 23/253 R |
| 4,039,286 A | | 8/1977 | Keller et al. | 23/230 |

(List continued on next page.)

FOREIGN PATENT DOCUMENTS

| | | | |
|---|---|---|---|
| EP | 0723812 | 7/1996 | |
| EP | 0744023 | 8/1997 | G01N/27/447 |
| EP | 0810030 | 12/1997 | B01L/7/00 |
| EP | 0812621 | 12/1997 | B01L/7/00 |
| EP | 0831330 | 3/1998 | |
| EP | 0488769 | 4/1998 | C12Q/1/68 |

*Primary Examiner*—Jill Warden
*Assistant Examiner*—Kathryn Bex
(74) *Attorney, Agent, or Firm*—Paul D. Asger; David J. Schodin

(57) ABSTRACT

A method of performing a determination of an item of interest in a sample using a single structure is disclosed. A sample is provided accessible to the single structure. A first container for processing the sample is placed in a first process path on the single structure. The sample is transferred to the first container in the first process path. A reagent is added to the first container in the first process path. Contents of the first container is mixed in the first process path. The item of interest in the sample is separated from the contents of the first container in the first process path. The separated item of interest in the sample is transferred from the first container in the first process path to a second container in a second process path on the single structure. Contents of the second container is brought to a first temperature different from a temperature of the first process path in the second process path. The item of interest in the second container is detected in the second process path.

11 Claims, 29 Drawing Sheets

U.S. PATENT DOCUMENTS

| | | | |
|---|---|---|---|
| 4,052,161 A | * 10/1977 | Atwood et al. | 23/230 R |
| 4,383,041 A | * 5/1983 | Kutsusawa et al. | 435/291 |
| 4,678,752 A | * 7/1987 | Thorne et al. | 435/291 |
| 4,683,195 A | 7/1987 | Mullis et al. | 435/6 |
| 4,683,202 A | 7/1987 | Mullis | 435/91 |
| 4,708,886 A | 11/1987 | Nelson | 422/72 |
| 4,737,464 A | 4/1988 | McConnell et al. | 436/43 |
| 4,774,055 A | 9/1988 | Wakatake et al. | 422/64 |
| 4,800,159 A | 1/1989 | Mullis et al. | 435/172.3 |
| 4,811,218 A | 3/1989 | Hunkapiller et al. | 364/413.01 |
| 4,935,040 A | 6/1990 | Goedert | 55/197 |
| 4,965,188 A | 10/1990 | Mullis et al. | 435/6 |
| 4,969,938 A | 11/1990 | America | 55/386 |
| 4,981,801 A | 1/1991 | Suzuki et al. | 435/290 |
| 5,008,182 A | 4/1991 | Sninsky et al. | 435/5 |
| 5,038,852 A | 8/1991 | Johnson et al. | 165/12 |
| 5,176,203 A | 1/1993 | Larzul | 165/61 |
| 5,215,714 A | * 6/1993 | Okada et al. | 422/64 |
| 5,229,297 A | 7/1993 | Schnipelsky et al. | 436/94 |
| 5,298,392 A | 3/1994 | Atlas et al. | 435/600 |
| 5,302,349 A | 4/1994 | Dandliker et al. | 422/82.08 |
| 5,318,748 A | * 6/1994 | Babson et al. | 422/72 |
| 5,333,675 A | 8/1994 | Mullis et al. | 165/12 |
| 5,411,876 A | 5/1995 | Bloch et al. | 435/91.2 |
| 5,432,096 A | 7/1995 | Zhu | 436/171 |
| 5,443,791 A | 8/1995 | Catheart et al. | 422/65 |
| 5,475,487 A | 12/1995 | Mariella, Jr. et al. | 356/336 |
| 5,475,610 A | 12/1995 | Atwood et al. | 364/500 |
| 5,480,614 A | 1/1996 | Kamahori | 422/70 |
| 5,498,392 A | 3/1996 | Wilding et al. | 422/68.1 |
| 5,525,300 A | 6/1996 | Danssaert et al. | 422/99 |
| 5,527,510 A | 6/1996 | Atwood et al. | 422/104 |
| 5,578,270 A | 11/1996 | Reichler et al. | 422/67 |
| 5,589,136 A | 12/1996 | Northrup et al. | 422/102 |
| 5,602,756 A | 2/1997 | Atwood et al. | 364/500 |
| 5,639,423 A | 6/1997 | Northrup et al. | 122/50 |
| 5,646,039 A | 7/1997 | Northrup et al. | 435/287.2 |
| 5,656,493 A | 8/1997 | Mullis et al. | 435/286.1 |
| 5,658,799 A | 8/1997 | Choperena et al. | 436/50 |
| 5,674,742 A | 10/1997 | Northrup et al. | 435/286.5 |
| 5,675,700 A | 10/1997 | Atwood et al. | 392/382 |
| 5,698,450 A | 12/1997 | Ringrose et al. | 436/526 |
| 5,720,923 A | 2/1998 | Haff et al. | 422/68.1 |
| 5,736,314 A | 4/1998 | Hayes et al. | 435/4 |
| 5,736,410 A | 4/1998 | Zarling et al. | 436/172 |
| 5,738,997 A | 4/1998 | Hayashi et al. | 435/7.4 |
| 5,741,708 A | 4/1998 | Carey et al. | 436/49 |
| 5,746,978 A | 5/1998 | Bienhaus et al. | |
| 5,779,977 A | 7/1998 | Haff et al. | 422/68.1 |
| 5,779,981 A | 7/1998 | Danssaert et al. | 422/99 |
| 5,786,182 A | 7/1998 | Catanzariti et al. | |
| 5,795,547 A | 8/1998 | Moser et al. | 422/104 |
| 5,804,384 A | 9/1998 | Muller et al. | 435/6 |
| 5,827,478 A | 10/1998 | Carey et al. | 422/64 |
| 5,827,480 A | 10/1998 | Haff et al. | 422/68.1 |
| 5,840,573 A | 11/1998 | Fields | 435/287.2 |
| 5,846,491 A | 12/1998 | Choperena et al. | 422/67 |
| 5,849,208 A | 12/1998 | Hayes et al. | 216/94 |
| 5,849,247 A | 12/1998 | Uzan et al. | 422/65 |
| 5,861,124 A | 1/1999 | Hosoi et al. | 422/82.08 |
| 5,861,256 A | 1/1999 | Glass et al. | 435/6 |
| 5,885,529 A | 3/1999 | Babson et al. | 422/65 |
| 5,885,530 A | 3/1999 | Babson et al. | 422/65 |
| 5,897,842 A | 4/1999 | Dunn et al. | 422/131 |
| 5,928,907 A | 7/1999 | Woudenberg et al. | 435/91.2 |
| 5,935,522 A | 8/1999 | Swerdlow et al. | 422/70 |
| 5,955,030 A | 9/1999 | Pettit | 422/82.08 |
| 5,955,351 A | 9/1999 | Gerdes et al. | 435/287.2 |
| 5,958,349 A | 9/1999 | Petersen et al. | 422/198 |
| 5,972,716 A | 10/1999 | Ragusa et al. | 436/172 |
| 5,985,217 A | 11/1999 | Krulevitch et al. | 422/99 |
| 6,022,746 A | * 2/2000 | Fritchie et al. | 436/50 |

* cited by examiner

STRUCTURE AND METHOD FOR PERFORMING A DETERMINATION OF AN ITEM OF INTEREST IN A SAMPLE

REFERENCE TO RELATED APPLICATION

This case is a conversion of provisional patent application, serial No. 60/104,191, filed on Oct. 14, 1998.

BACKGROUND

The following relates generally to a structure and a method for determining an item of interest in a sample. More specifically, the following relates to determining an item of interest that may be or include all or portions of a specific region of DNA, RNA, fragments, complements, peptides, polypeptides, enzymes, prions, proteins, messenger RNA, transfer RNA, mitochondrial RNA or DNA, antibodies, antigens, allergens, parts of biological entities such as cells, virons or the like, surface proteins, functional equivalents of the above, etc.

To provide information about a patient's health, a number of tests can be performed on a patient sample, such as the patient's bodily fluids. These bodily fluids may include serum, whole blood, urine, swabs, plasma, cerebra-spinal fluid, lymph fluids, tissue solids, etc. The tests performed on the patient's bodily fluids can determine an item of interest, such as those stated above, in the bodily fluids. Based on the determination of the item of interest in the patient's bodily fluids, information about the patient's health status can be obtained.

SUMMARY

One embodiment described herein provides a method of performing a determination of an item of interest in a sample using a single structure. A sample is provided accessible to the single structure. A first container for processing the sample is placed in a first process path on the single structure. The sample is transferred to the first container in the first process path. A reagent is added to the first container in the first process path. Contents of the first container is mixed in the first process path. The item of interest in the sample is separated from the contents of the first container in the first process path. The separated item of interest in the sample is transferred from the first container in the first process path to a second container in a second process path on the single structure. Contents of the second container is brought to a first temperature different from a temperature of the first process path in the second process path. The item of interest in the second container is detected in the second process path.

In another method, a sample is transferred to a first container in a first process path on a single structure. An item of interest in the sample is separated from the contents of the first container in the first process path. The separated item of interest in the sample is transferred from the first container in the first process path to a second container in a second process path on the single structure. Contents of the second container is brought to a first temperature different from a temperature of the first process path in the second process path. The item of interest is detected in the second container in the second process path.

In an additional method, a sample is transferred to a container in a process path on the single structure. An item of interest in the sample is separated from the contents of the container in the process path. Contents of the container is brought to a first temperature in the process path. Contents of the container is brought to a second temperature different from the first temperature in the process path. The item of interest is detected in the container in the process path.

In a further method, a sample is transferred to a first container in a first process path on the single structure. The sample is transferred from the first container in the first process path to a second container in a second process path on the single structure. Contents of the second container is brought to a first temperature different from a temperature of the first process path in the second process path. The item of interest is detected in the second container in the second process path.

In yet a further method, a sample is transferred to a container in a process path on the single structure. Contents of the container is brought to a first temperature on the process path on the single structure. Contents of the container is brought to a second temperature different from the first temperature in the process path on the single structure. The item of interest is detected in the container in the process path on the single structure.

DETAILED DESCRIPTION OF ILLUSTRATED EMBODIMENTS

Figure 1:
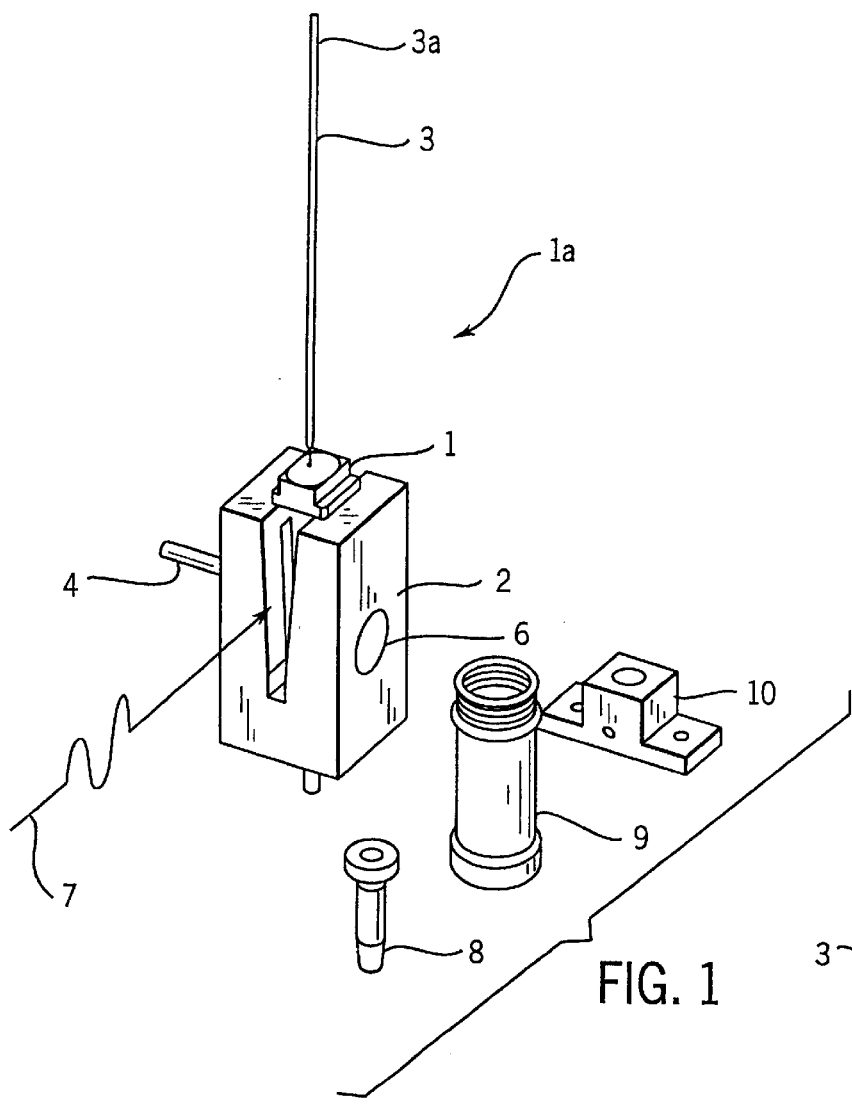
FIG. 1 is a perspective view of a structure described herein.

The embodiments described herein relate to methods and structures for determining an item of interest in a sample. The item of interest may be a specific region or regions of DNA or RNA, or may be fragments, complements, peptides, polypeptides, enzymes, prions, proteins, messenger RNA, transfer RNA, mitochondrial RNA or DNA, antibodies, antigens, allergens, parts of biological entities such as cells, virons or the like, surface proteins, functional equivalents of any of these, concentrations of any of these or any other desired element of the sample. In an exemplary embodiment, the item of interest may be selected from, but is not limited to specific DNA or RNA regions, antibodies, or antigens including but not limited to, CT, CT/GC, MT, HCV, HBV, HPV, HIV, CMV, HLA, HTLV, and other items related, but not limited to, infectious diseases, genetic markers, cancers, cardiovascular items, pharmacogenetic items, etc. In some embodiments, the item of interest may be selected from, but not limited to antibodies to HCV, antibodies to HIV 1HIV 2, antibodies to hepatitis B core antigen (HBcAb), carcinoembryonic antigen (CEA), cancer antigen 19-9 (CA19-9), Hepatitis B Surface Antigen (HBsAg), antibodies to Hepatitis B Surface antigen (HBsAb), alpha-fetoprotein (AFP), Total prostate specific antigen (Total PSA), Free PSA, Thyroid stimulating Hormone (TSH), luteinizing hormone (LH), follicle stimulating hormone (FSH), beta human chorionic gonadotropin (B-hCG), Free Thyroxine (Free T4), Free triiodothyronine (Free T3), Total T4, Total T3, Progesterone, Testosterone, Estradiol, Prolactin, vitamin B12 (B12), Folate, Glycated Hemoglobin, and Ferritin. In essence, almost anything can be the item of interest.

The structures and methods described herein may be employed in a number of different configurations. For the sake of clarity of understanding, the structures and methods will be discussed with respect to their employment in a DNA/RNA sample preparation, amplification, and detection analyzer which performs approximately 100 or more determinations of items of interest in a sample in an hour, or if the sample preparation is divided, approximately 300 or more determinations of items of interest in a sample in an hour. Alternately, the same structure may be used as an immunoassay analyzer or as both an immunoassay analyzer and DNA/RNA analyzer. It is to be noted that the structures and methods can be used in other employments, such as in analyzers which perform 600, 400, 200, 50, etc. determinations in an hour.

A number of structures may be joined together or integrated to meet individual needs, such as modifying the number of tests performed in a given time period (throughput), tailoring the items of interest to be determined, etc. For example a number X of structures which perform Y determinations in a given hour may be connected such that the connected structures perform XY determinations in an hour. If desired, the resources of the structures may be allocated in a manner substantially similar to that disclosed in co-pending U.S. patent application, Ser. No. 09/041,352 filed on Mar. 12, 1998. That application is assigned to the assignee of the present case and the disclosure thereof is incorporated herein in its entirety.

In other embodiments, one or more structures may be operatively connected with another analyzer, such as an immunoassay analyzer (e.g. disclosed in U.S. Pat. No. 5,795,784 referenced below), a blood analyzer (e.g. disclosed in U.S. Pat. No. 5,891,734 referenced below), and the like.

It is to be noted that all such structures may perform all similar determinations of items on interest in substantially the same way. For instance, all determination process steps for all similar items of interest may be performed within the same time frame, such as 36 seconds, irrespective of the number of determinations to be performed by the given structure. These structures may include common elements, such as reagents, disposable articles, other elements, such as fluids and the like, delivery technologies, determination step performance mechanisms, software, etc.

In other applications, the structure may be joined, e.g. with a conveyor system and the like, along with supporting hardware and software, such that the structure can be used with different structures or analyzers, such as clinical chemistry or hematology analyzers and the like, in the same setting. This conveyor system may move samples among the structures such that different determinations can be made with respect to one sample. Also, while operation of the structure is described herein with respect to only one structure, for the sake of clarity, it is to be remembered that multiple structures can operate in the same or in different fashion, either simultaneously or at different times. Furthermore, steps of one method of operation can be combined with steps of another method of operation to arrive at yet more methods of operation.

Any of the structures or methods described herein may be combined, in any suitable fashion, with the structures or methods or portions thereof described in currently available literature, such as the following United States Patents. As all of these patents are assigned to the assignee of the present case, the disclosures of those patents are incorporated herein in their entirety. The United States Patents are: U.S. Pat. Nos. 5,468,646, 5,536,049, 5,543,524, 5,545,739, 5,565,570, 5,669,819, 5,682,662, 5,723,795, 5,795,784, 5,783,699, 5,856,194, 5,859,429, 5,891,734, and 5,915,583.

Construction of structures described herein is intended to analyze specimens for various items of interest in a cost-effective way. The structures allow a user to supply a sample to the structure, to have the structure process, e.g. incubate, prepare, lyse, elute, analyze, read, etc., the sample and to have the structure report a result of the process. Structure sub-components include apparatus and methods of mixing, aspiration and dispense of materials, such as samples and reagents, incubation, chemistry separation, and detection, just to name a few. In general terms, structure construction implementation for chemistry automation may be driven by many factors such as desired patient sample addition methods, reagent addition methods, throughput (number of determinations per given time period), contamination reduction methods, detection methods, degree of mixing, and incubation temperature and duration needs.

Figure 12A:
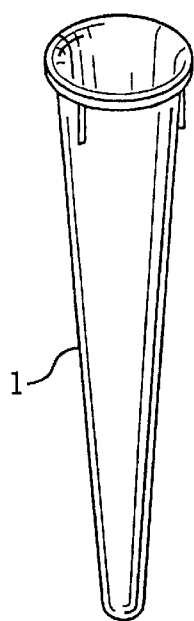
FIGS. 12A through 12O are perspective views of various embodiments of the container shown in FIG. 1.
Figure 12B:
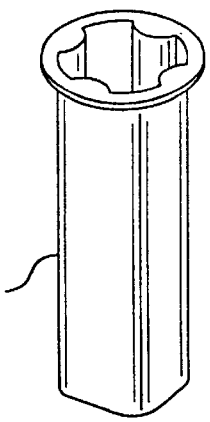
Figure 12C:
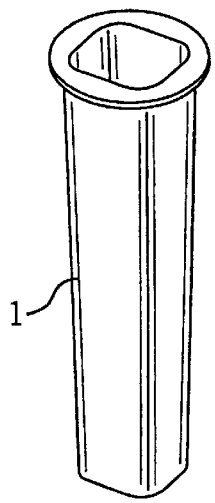
Figure 12D:
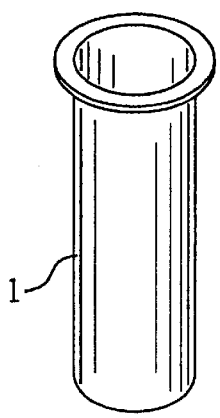
Figure 12E:
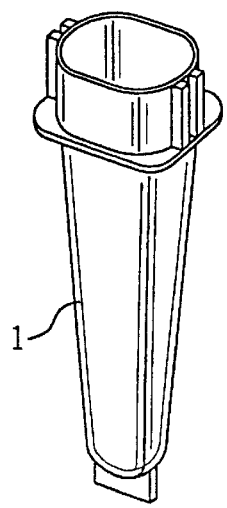
Figure 12F:
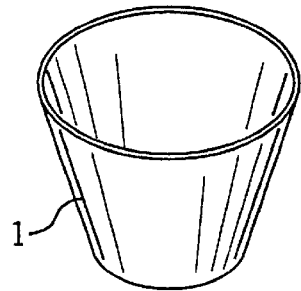
Figure 12G:
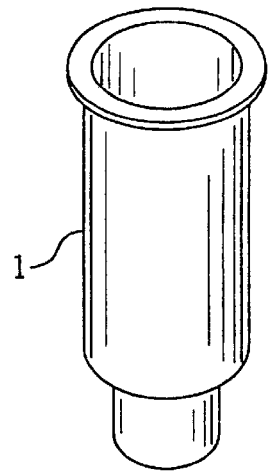
Figure 12H:
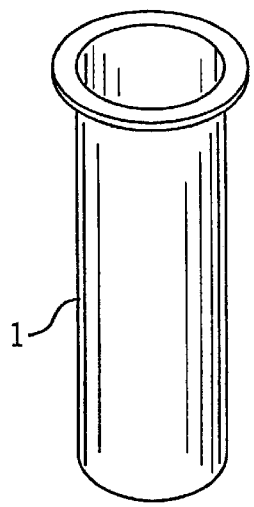
Figure 12:
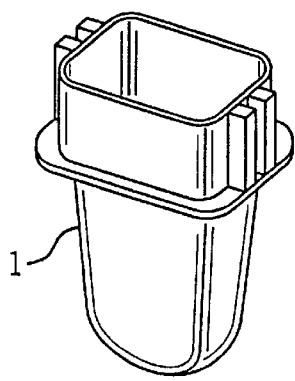
Figure 12J:
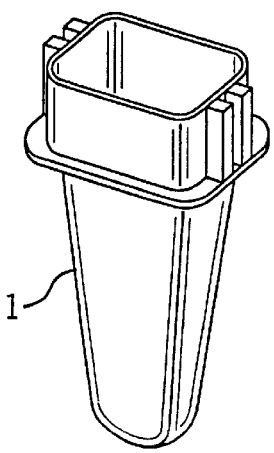
Figure 12K:
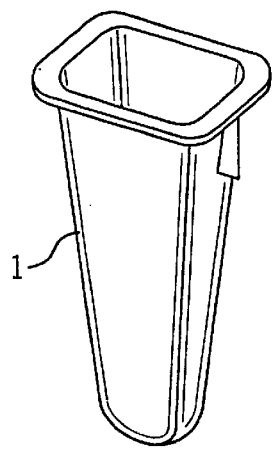
Figure 12L:
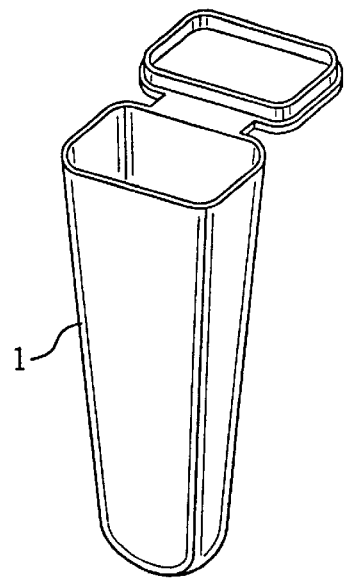
Figure 12M:
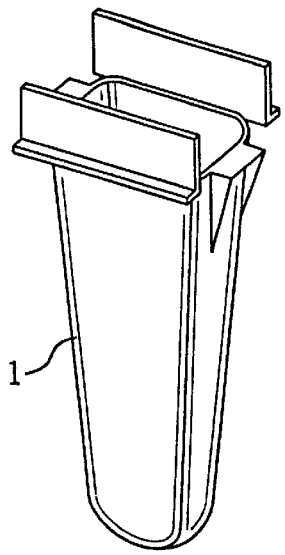
Figure 12N:
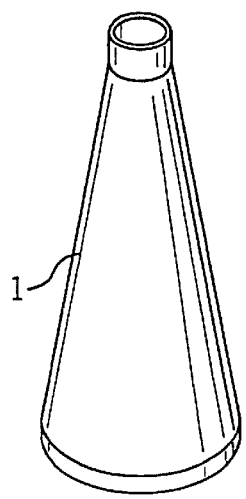
Figure 12:
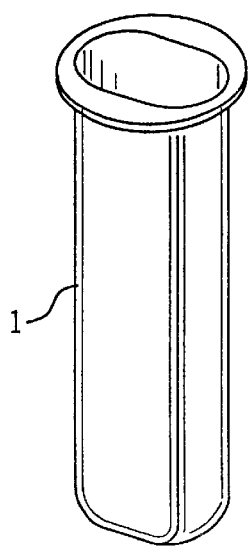

FIG. 1 discloses a structure 1a amenable to a relatively decreased throughput, such as about 1 determination per every 1.5 hours, environment. The structure 1a comprises a first container 1 removably placed in a base 2. In some embodiments, the base 2 may have a construction substantially similar to constructions of the process path disclosed in above-referenced U.S. Pat. No. 5,795,784, in which case, the structures illustrated in FIGS. 1 and 2 can be disposed at appropriate locations along the process path. Probe 3 is attached to a suitable prime mover such that the probe 3 can move in multiple directions, if desired. The probe 3 is fluidly connected at location 3a to suitable structures which enable the probe 3 to perform aspiration and dispense functions. These fluidic functions could be implemented with use of common pump (e.g. syringe, peristaltic, etc.) and valve technology, some of which is well understood today. The probe 3 can be moved by one of many means such as a Tecan gantry (Tecan RSP model series, Tecan Switzerland), an Abbott theta-Z robot (part number 78479, Abbott Laboratories, Abbott Park Ill.) or the like. Base 2 could be fabricated out of any desirable material, such as machined and coated aluminum and the like. In an exemplary embodiment, the base 2 is made with 6061-T6 aluminum with a MIL-A-63576 Type I finish. The first container 1 could be fabricated out of any desirable material, and may be molded out of a polyethlyne (DOW 30460M HDPE or Chevron 9512, for example) or polypropylene (Montel PD701N, for example), or polystyrene (Dow 666, for example). In the illustrated embodiment, the first container 1 is sized to contain an amount, such as about 7 mL, of fluid, such as sample and reagent. FIGS. 12A through 12P show alternative constructions of the first container 1.

Figure 2:
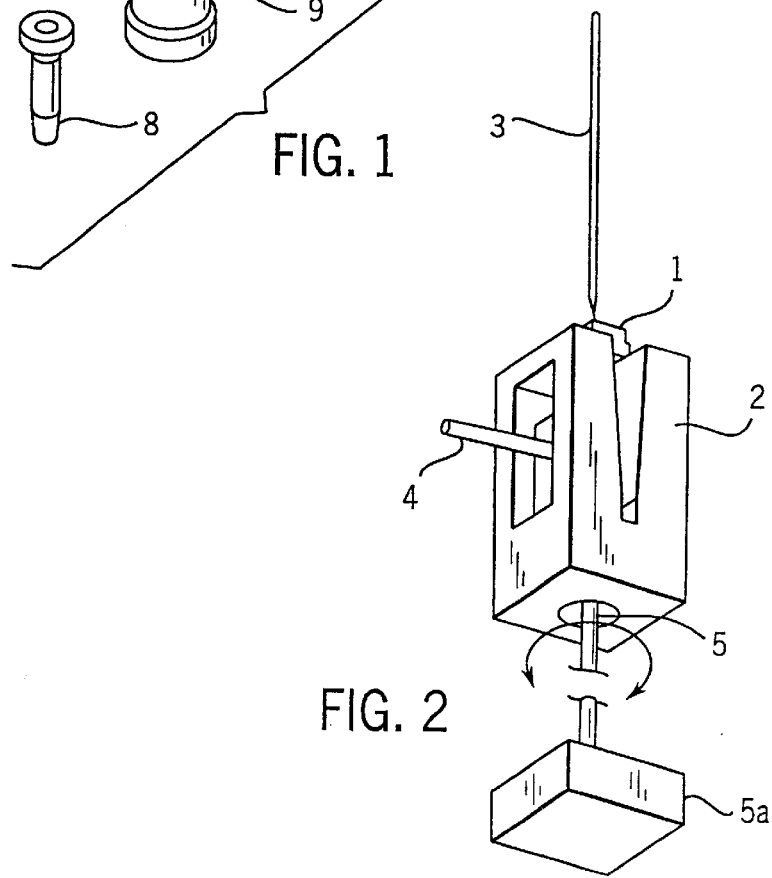
FIG. 2 is a perspective view of the structure of FIG. 1.

It is to be noted that the construction of the base 2 may be modified to accommodate or complement various constructions of the first container 1 as the base 2 provides features to accept first container 1 and to house a retractable magnet 4 shown in FIGS. 1 and 2.

Magnet 4 can be moved with respect to the first container 1 at selected times during performance of a given determination of an item of interest in a sample in the first container 1. The movement of the magnet 4 can effect performance of a step in the determination process thereby allowing that step to be selectively automatically performed or avoided as desired. In one embodiment, the magnet 4 may be moved relatively proximate to the container to attract magnetically responsive particles within the first container 1 to a side wall of first container 1 thereby separating those particles which may be bound with a desired item of interest in a patient sample from the remaining patient sample or other contents of the first container 1.

Before, during or after such magnet 4 induced separation, probe 3 may aspirate a portion of the first container 1 contents to waste/wash reservoir 10. Subsequent dispense, separation, and aspiration steps may be employed to enhance the item of interest determination. During periods of the determination where magnetic separation is not desired, i.e. the magnetic separation step is avoided, magnet 4 may be moved relatively distally with respect to the first container 1 to reduce effects of the magnetic field of the magnet 4 on the first container 1 and its contents. If desired, magnetically responsive particles to which no item of interest is attached may be attracted to the side wall of the first container 1 while the remaining contents, possible containing an item of interest, of the first container 1 is removed from first container 1, such as by the probe 3.

In some embodiments, a thermal regulation device (heating and/or cooling) 7 can be provided with the base 2. The device 7 may be manually or automatically removably connected with the base 2, may be operated by an appropriate controller, such as a computer having memory running appropriate routines, and may utilize currently available thermal transfer means of conduction, convection, and/or radiation, etc. In one embodiment, thermally regulated (heated and/or chilled) air is moved with respect to the first container 1 to thermally regulate first container 1 contents in a desired manner.

At various times during performance of a given determination of an item of interest, a sample disposed in container 8 and reagent contained in container 9 may be added to first container 1, such as by probe 3. If multiple samples and/or reagents are desired, an array, such as a conveyor, a carousel, other movable arrangement, possibly recirculating, or the like, of multiple containers 8 and/or 9 could be provided. Containers 8 and 9 could be fabricated out of any suitable material, such as a polymer like polystyrene (DOW 666), high-density polyethylene (DOW 30460M HDPE or Chevron 9512) respectively, and the like.

To increase preservation of the contents of either container 8 or 9, a cover 30 (FIG. 5C), substantially similar to the cover disclosed in U.S. Pat. No. 5,795,784 referenced above, could be added to either container 8 or 9. The cover 30 may be made from any suitable material, such as Lexington Medical 3481005 EPDM, Abbott EPDM (Ashland, Ohio) and the like. Some constructions for containers 8 and 9 and associated covers can be found in U.S. Pat. Nos. Des. 401,697, 401,699, and 397,938 respectively, referenced above. A method for fitting a container such as container 8, to other containers or a carrier is described in commonly owned U.S. Pat. No. 5,915,583.

Figure 5A:
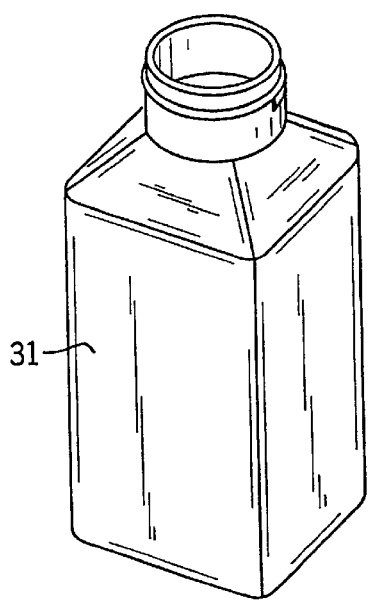
FIGS. 5A through 5F are perspective views of elements for use with the structure shown in FIGS. 3A and 3B.
Figure 5B:
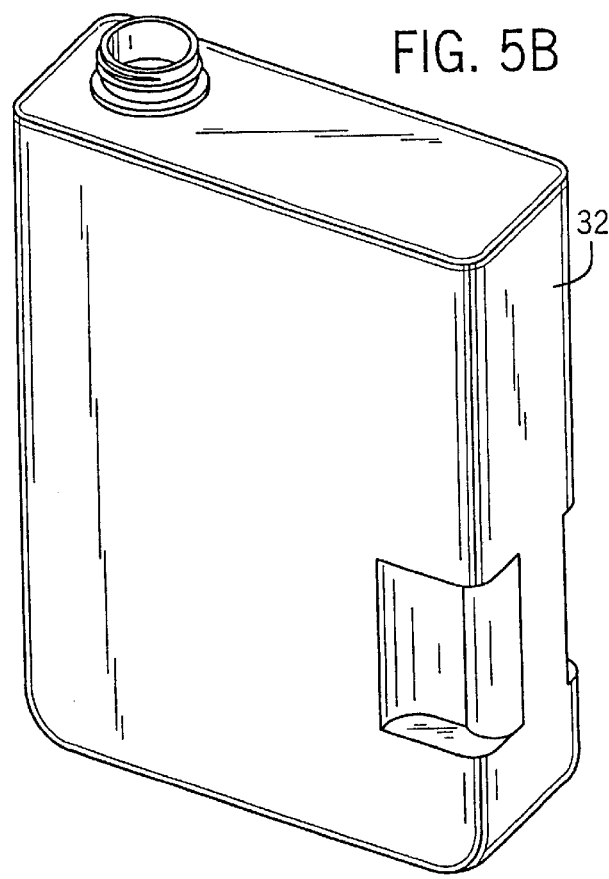
Figure 5C:
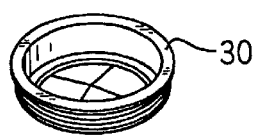
Figure 5D:
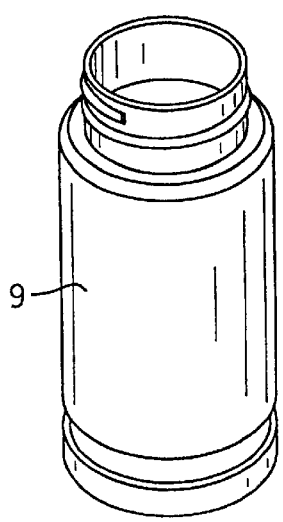

Once sample and/or reagent is added to first container 1, probe 3 may be washed, i.e. likelihood of exposure to a contaminant is reduced, by moving the probe 3 to waste/wash reservoir 10 for a fluid rinse of the probe 3. In other embodiments, probe 3 could be modified to incorporate a disposable tip, such as the pipettor tip disclosed in U.S. Pat. No. 5,232,669 (assigned to the assignee of the present case and incorporated herein in its entirety by this reference). After intended use of the pipettor tip, the tip may be ejected from a fluidic/transport interface with the probe 3 to waste. Another example of a disposable tip 28 is illustrated in FIG. 5F.

A bore 6 is disposed on the base 2 to accommodate a detector, such as a photomultiplier tube, a photodiode and the like. In the illustrated embodiment, the bore 6 is located opposite magnet 4 in a similar fashion to the like structures disclosed in U.S. Pat. No. 5,795,784. Thus, similar operations, such as detection of chemiluminescence or other signal generated by a label, such as a fluorophore and the like, are possible.

Figure 13:
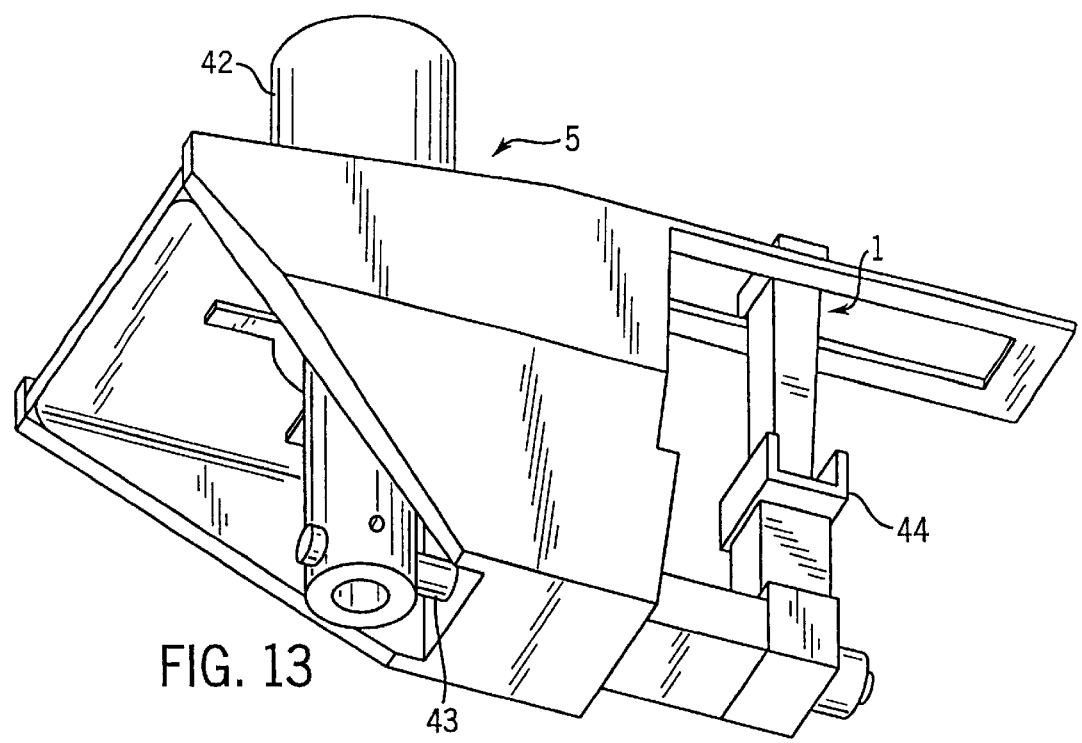
FIG. 13 illustrates engagement of the container of FIG. 12E with a mixer.

A mixer 5, illustrated in FIG. 2, is also provided on the base 2. The mixer 5 is coupled to a driver 5a that applies force to the mixer 5, possibly inducing an orbital motion on the first container 1 thereby causing mixing of first container 1 contents at desired times. The base 2 is constructed to limit first container 1 degrees of freedom important to the mixing process. Base 2 may include a lid to assist in controlling degrees of freedom important to the mixing process. FIG. 13 shows an alternate construction of mixer 5. An additional embodiment of a suitable mixer is disclosed in U.S. Pat. No. 5,795,784.

If desired, the structure 1a shown in FIG. 1 can be modified to perform a larger number of determinations, such as about 100, in a given time period, i.e. a relatively increased throughput environment. The structure 1a could be operatively connected with one or more additional structures 1a, each of which possessing one or more of the probe 3, magnet 4, mixer 5, bore 6 for a detector, and the thermal regulation device 7. In this embodiment, the multiple structures 1a permit selective activation of magnet 4, detector 6, heat/cooling elements 7, mixer 5, sample and reagent aspirations and dispenses, etc. at desired times during the determination process, viz. the steps executed by those elements are selectively automatically performed. With this arrangement, a determination of an item of interest in a sample can be conducted over more than one position or with more than one structure 1a, thereby allowing at least two samples to be processed substantially simultaneously.

To streamline operative connection of multiple structures 1a, a transport system, such as a conveyor (bounded or endless), a carousel or the like, could be used to move first container 1 from one structure 1a to another. The transport system may be substantially similar to the process path disclosed in the above-referenced '784 patent. Depending on location of the structure(s) 1a, the transport system and/or the individual structures can be constructed to provide only the functions desired to be performed at a given time in a determination. For example, a relatively large number, such as 100, structures 1a could be operatively connected together and only a subset, such as 5, of the structures 1a may include a mixer 5.

Figure 9:
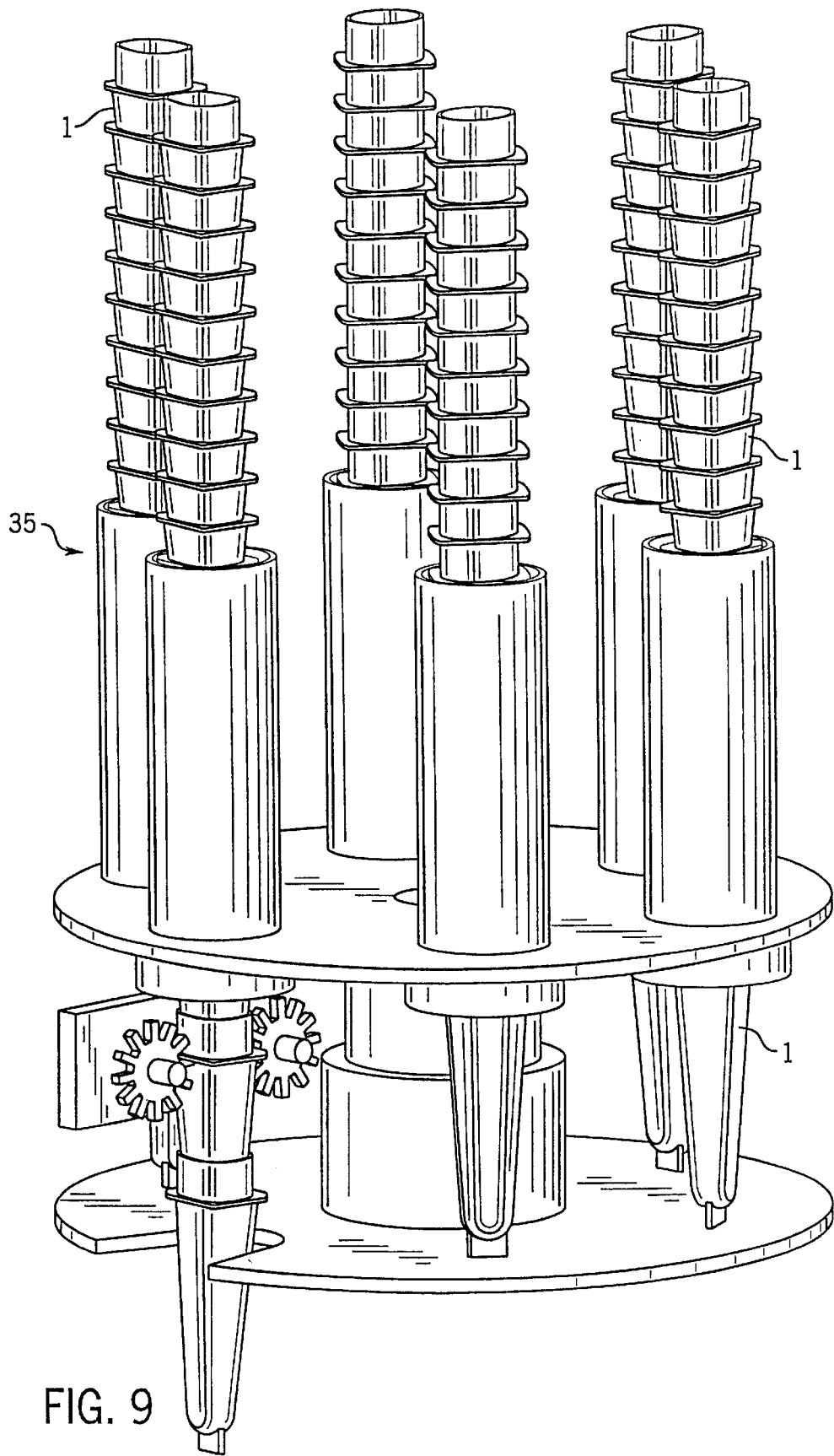
FIG. 9 is a perspective view of a container loader for use with the structure of FIGS. 3A and 3B.
Figure 18:
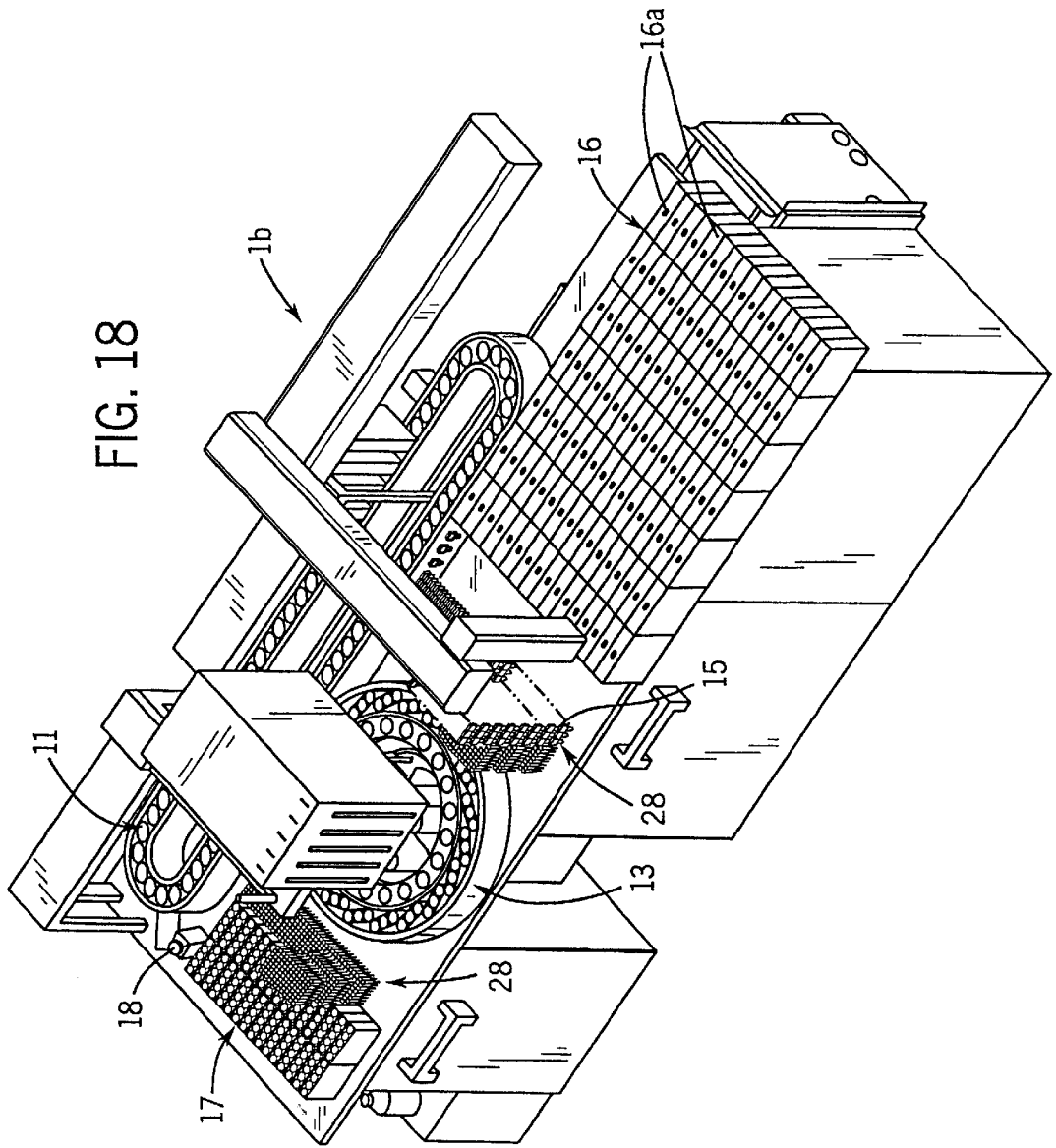
FIG. 18 is an isometric view of a structure substantially similar to the structure of FIGS. 3A and 3B.

FIGS. 3 and 18 show a structure 1b essentially comprising a plurality of structures 1a located substantially adjacently. In this embodiment, containers 1 are loaded substantially automatically onto a first process path 11 from a container loader and transport 35 illustrated in FIG. 9. Alternately, first container 1 could be loaded manually or automatically in a fashion described in the '784 patent. Containers 1 are moved, possibly one position every selected time interval, such as every 36 seconds, through the first process path 11 to various locations along the first process path 11 where various operations, such as reagent addition, sample addition, incubation, mixing, washing and the like, are selectively automatically performed according to requirements of the intended format or protocol of the determination being performed. In an exemplary embodiment of the structure 1b, the first container 1 is moved approximately 1.2 inches along the first process path 11 about every 36 seconds.

The first process path 11 includes at least one temperature controller or heater to keep the first process path 11 at a desired temperature. The first process path 11 may be kept at one temperature or any desired number of temperatures, such as with multiple heaters. In one embodiment, the heater maintains the first process path 11 at about 37 degrees Celsius. In another embodiment, one portion of the first process path 11 may be maintained at about 37 degrees Celsius while another portion of the first process path may be maintained at about 70 degrees Celsius.

Various methods may be implemented to heat the first process path 11 to at least one temperature while isolating the container 1 maintained at the least one temperature from other temperatures. For example, in one embodiment, the first process path 11 may be used to perform a first incubation, such as lysis for about 20 minutes at about 37 degrees Celsius, and a second incubation, such as elution for about 20 minutes at about 50 degrees Celsius, with container 1. Container 1, being used for both lysis and elution on the first process path 11, can be thermally isolated from the second temperature while the container 1 is exposed to the first temperature, and vice versa.

If the first process path 11 were made of a suitable material, such as aluminum and the like, and if the first process path 11 were heated, e.g. conductively, to the first temperature or the second temperature at an appropriate time, a member may be introduced to thermally insulate portions of the first process path 11 exposed to the first temperature from portions of the first process path 11 exposed to the second temperature. This member may be an insulating material, a physical barrier or the like. The member may be actively cooled or heated based on temperature conditions measured at the first process path 11 portions specific to the first temperature, e.g. 37 degrees Celsius, and specific to the second temperature, e.g. 50 degrees Celsius, thereby limiting exposure container 1 to the first or second temperature, as appropriate.

In another embodiment, the first process path 11 is maintained at a first temperature, for example 37 degrees Celsius. At a portion of the first process path 11, where it is desired to maintain a second temperature, for example 50 degrees Celsius, at least one other thermal energy source, such as an IR source and the like, may be thermally coupled with the first process path 11 to provide a desired amount of heat to the relevant portions of the first process path 11 at times required. Contents present in container 1 may experience a thermal rise to the second temperature during exposure to IR source followed by a thermal degradation to the first temperature as the container 1 is removed from exposure to the IR source.

Figure 10:
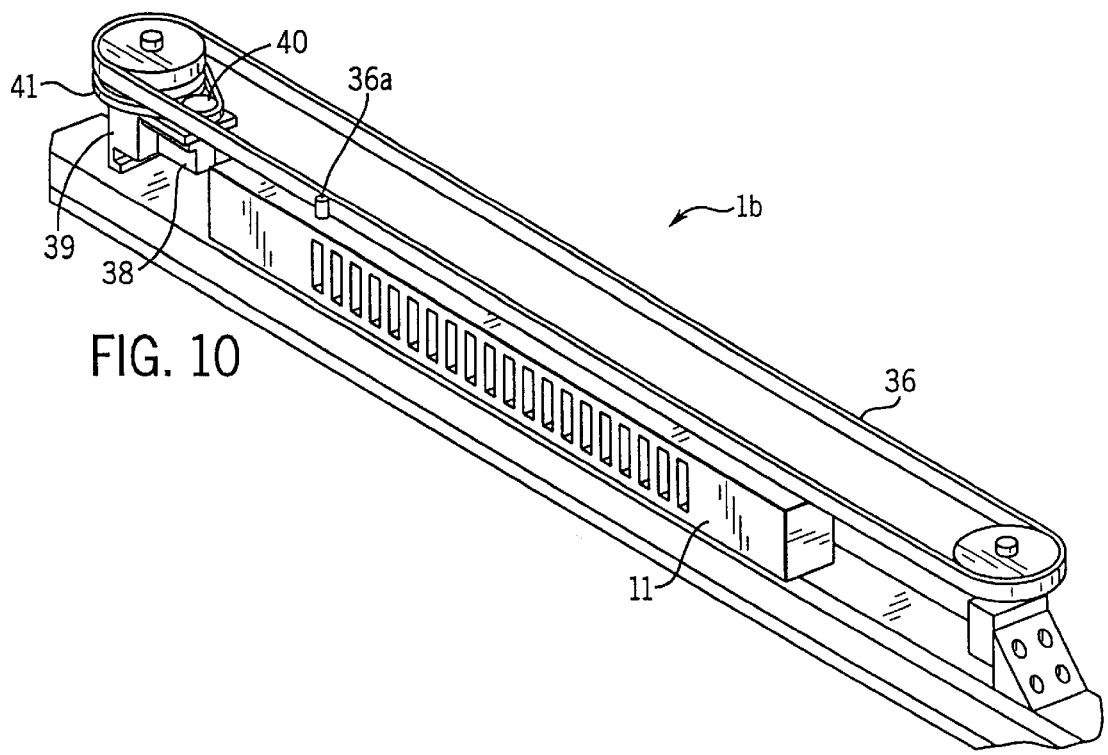
FIG. 10 is a perspective view of a container transporter for use with structure shown in FIGS. 3A and 3B.
Figure 11:
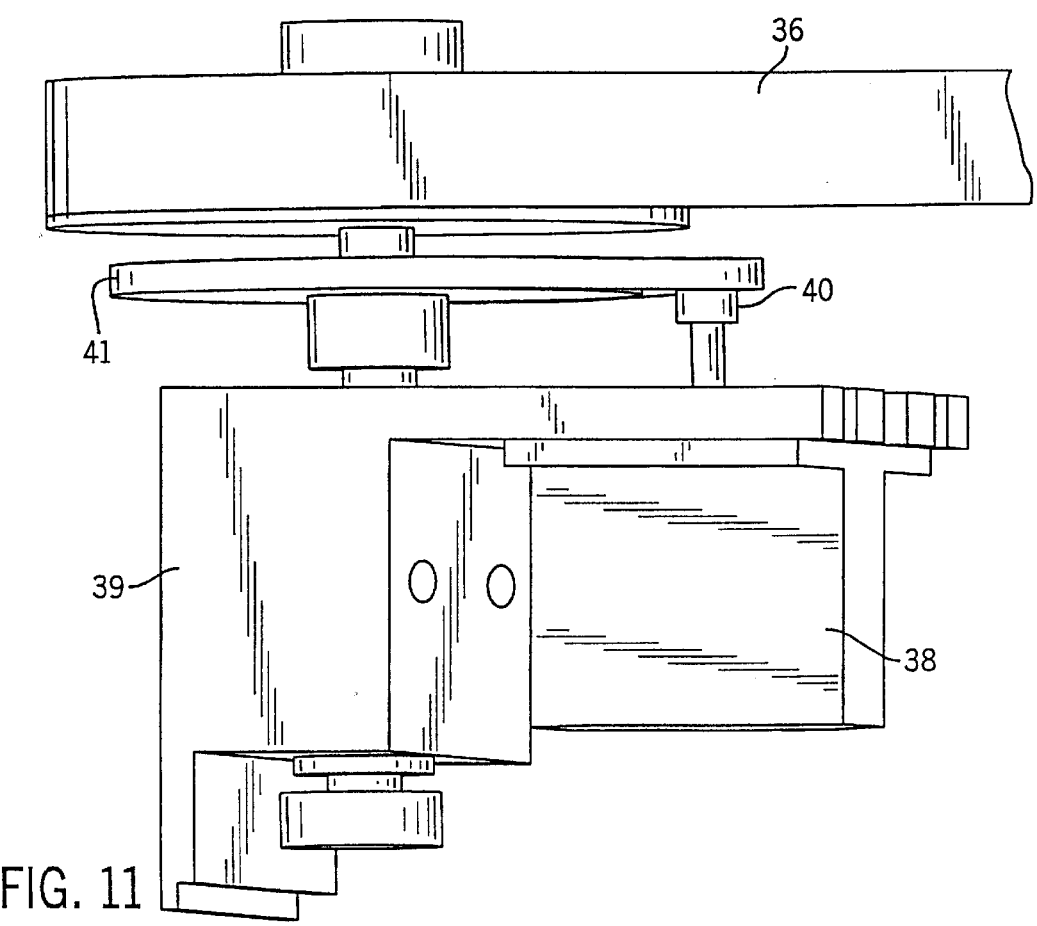
FIG. 11 is a magnified view of a portion of FIG. 10.

In another embodiment of the structure 1b illustrated in FIGS. 10 and 11, once a first container 1 is placed on the first process path 11, belt 36 moves first container 1 via engagement with pin 36a on the belt 36. Prime mover 38 engages belt 36 via drive gear 40 and driven gear 41. Prime mover mount 39 aligns prime mover 38 to driven gear 41 in the desired fashion.

Figure 6:
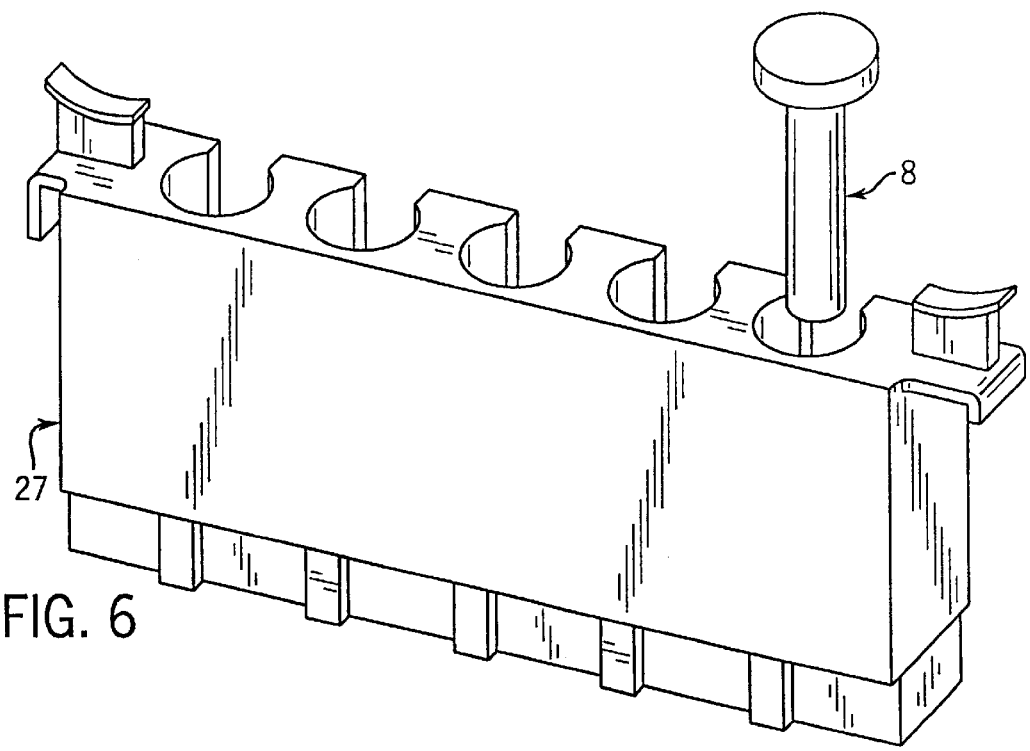
FIG. 6 is a perspective view of a container and a carrier for use with the structure of FIGS. 3A and 3B.

Returning to FIGS. 3A and 3B, samples disposed in containers 8, such as test tubes and the like, are loaded in container carriers 27 which are loaded onto input queue 17. Examples of a sample container 8 and an associated container carrier 27 are shown in FIG. 6. The container 8 and the container carrier 27 may be substantially similar to the container disclosed in above-referenced U.S. Pat. No. 5,915, 583 and U.S. Pat. Des. 401,697.

Input queue 17 may be constructed similarly to a sample handler like the currently available Abbott FPC Flexible Pipetting Center or the common structures described in the '784 patent. An example of an input queue 17 is shown in FIG. 4 and comprises a conveyor system like that disclosed in the '784 patent. The embodiment illustrated in FIG. 4 is constructed such that a structure, such as the structure 1b of FIGS. 3A and 3B, may be disposed in space 17a so that the input queue 17 and the structure 1b can cooperate. In this embodiment, sample input and output queues 17 and 17b, respectively, may be disposed adjacent to each other offset by a local queue 17c.

A bar code reader 25 is located adjacent the first process path 11 such that the bar code reader 25 can read a code associated with the container 8 and/or the container carrier 27. The bar code reader 25 is used to identify a given sample located on the input queue 17 at a position accessible by pipettor 19.

When the bar code reader 25 identifies a sample, pipettor 19 can transfer that sample from container 8 on the input queue to first container 1 located on the first process path 11. Other items, such as reagents and the like, may be added to first container 1 by pipettor 19 and pipettor 12 in accordance with a given determination format. Reagents are stored in reagent handler 13 which may be similar to the reagent carousel disclosed in the '784 patent. In an exemplary embodiment, pipettors 19 and 12 may add reagents to first container 1 at times specified in the "1 Tube DNA/RNA 20-20 Min Sample Prep Protocol, 1 Tube 1.5 hr PCR End Point Protocol" specified below.

In addition to pipettor 19 and 12, dispense nozzles (not shown for clarity) fluidly connected with appropriate pumping mechanisms may add reagents from bottles 29, 31, and 32 to first container 1 via fluid dispense nozzles. Containers 29, 31, and 32 are shown in FIGS. 5E, 5A, 5B and 19. In one embodiment, container 31 contains solid phase microparticles, possibly magnetically responsive, which may require an agitator to homogenize the container 31 contents, i.e. resuspend the particles in a fluid medium. The agitator may be incorporated into a microparticle reagent handler 18 shown in FIGS. 3A and 3B. This re-suspension could be accomplished with commonly understood mixing fins, complementary container fins and/or fin motion among other methods. In a specific embodiment, resuspension of the particles within container 31 is achieved with a stir bar and associated apparatus also commonly understood in the field. Some or all containers described herein may be placed on the structure 1b shown in FIGS. 3A and 3B. The contents of the containers may be preserved with use of reagent seal 30 shown in FIG. 5C and/or with use of refrigeration. To provide additional flexibility in dispensing reagents, reagent dispense nozzles operatively associated with the first process path 11 may be integrated with transport mechanisms to allow reagents to be dispensed at any desired position on the first process path 11.

Sometimes, it may be desirable to mix or to agitate the contents of first container 1. Mixing of first container 1 contents along first process path 11 may be selectively automatically performed at an selected time by a mixer 5, such as the mixer 5 shown in FIG. 13. In this embodiment, first container 1 is operatively engaged via feature 44 which is, in turn, operatively coupled to gear train 43. Gear train 43 is configured to induce motion, e.g. orbital, circular or other, to first container 1 when rotated by prime mover 42. In one embodiment, mixing occurs at times specified in the "1 Tube DNA/RNA 20-20 Min Sample Prep Protocol, 1 Tube 1.5 hr PCR End Point Protocol" specified below.

Figure 7:
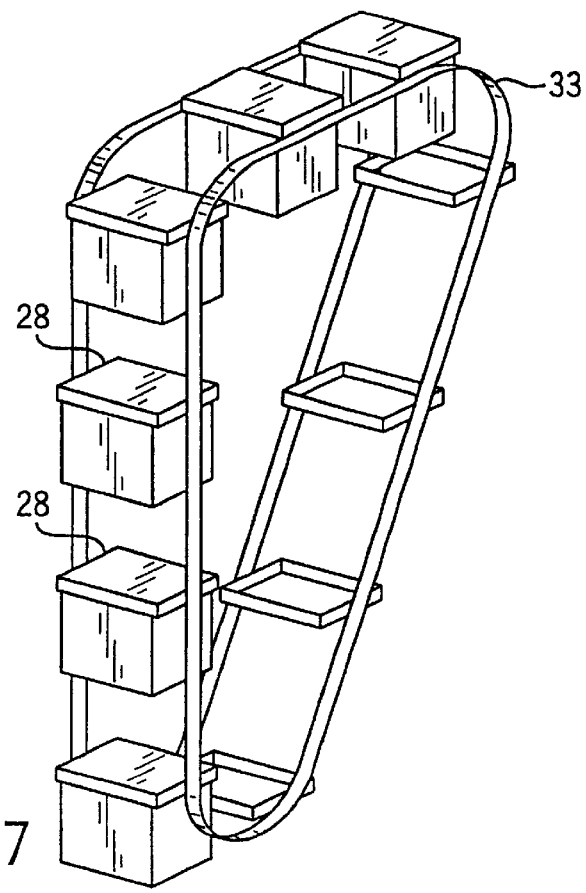
FIG. 7 is a perspective view of a pipette tip loader for use with the structure shown in FIGS. 3A and 3B.
Figure 8:
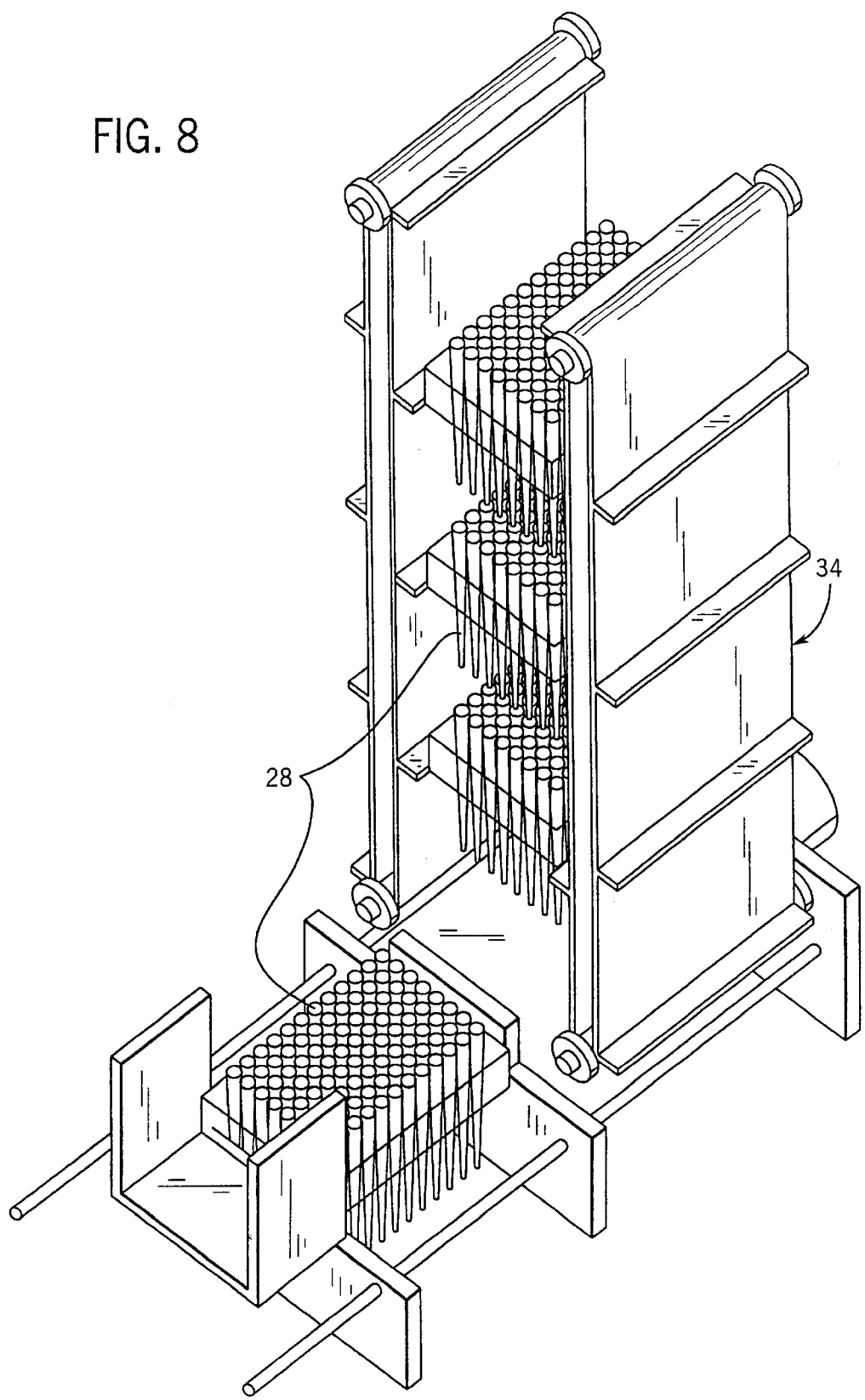
FIG. 8 is a perspective view of another embodiment of a pipette tip loader for use with the structure shown in FIGS. 3A and 3B.
Figure 19:
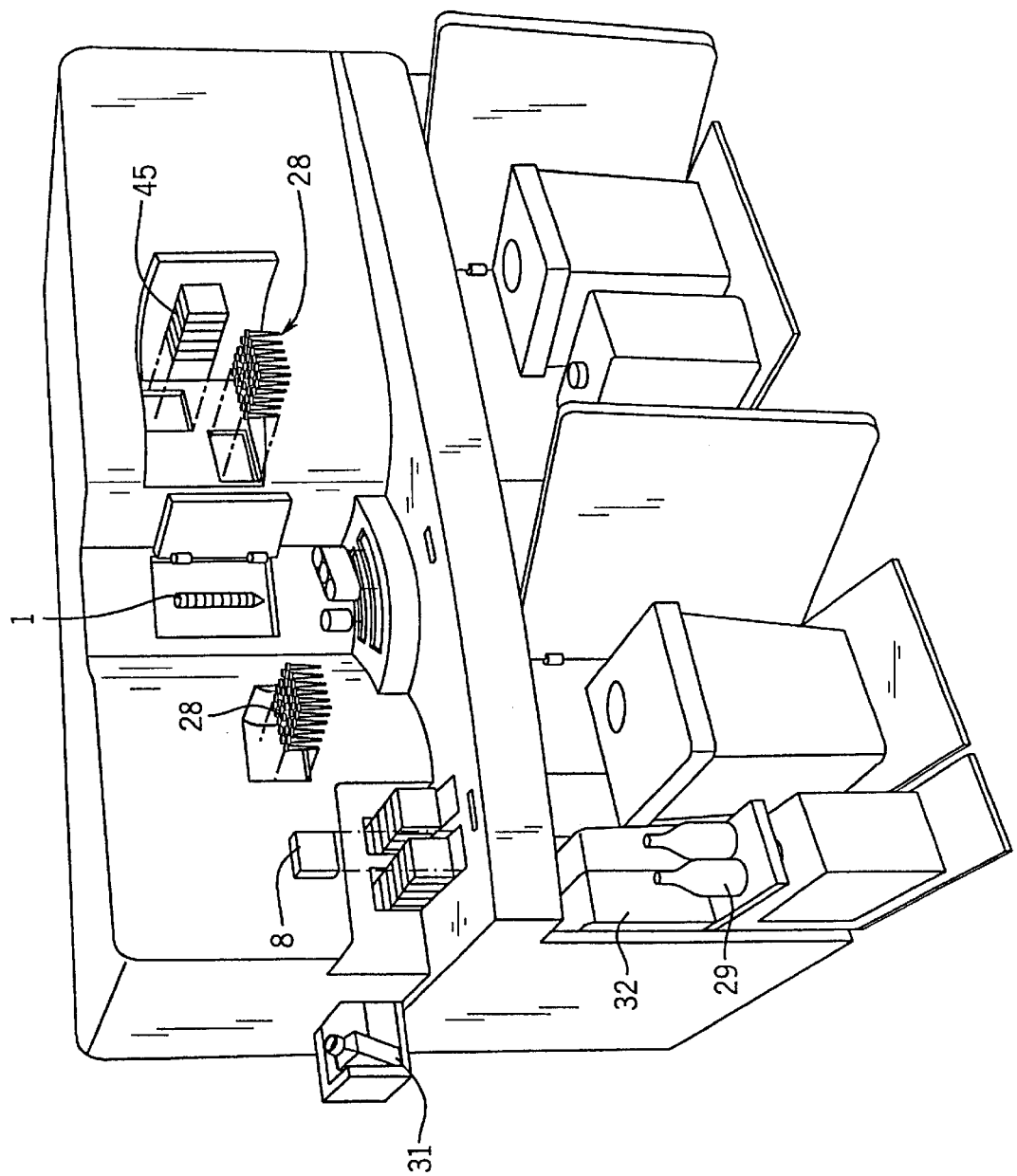
FIG. 19 is an isometric view of a structure substantially similar to the structure of FIG. 18.

In an embodiment where pipettors 19 and 12 are configured for use with disposable pipettor tips 28 shown in FIGS. 5F and 19, transport and loading of a tip 28 or a group of tips 28 may be accomplished with loader and transport mechanism 33 shown in FIG. 7, loader and transport mechanism 34 shown in FIG. 8 or other equivalent arrangements.

After engagement of a tip 28 by either pipettor 19 or 12, liquid level sensing (executed by any currently available method), aspiration from selected container(s), and dispense to first container 1 occurs. Pipettor 12 or 19 may include an apparatus which can detect a liquid level and/or temperature. This apparatus may include, but is not limited to, photo optics, capacitive members, IR, sonar, or other wave form generators. After dispense, tip 28 is washed with liquid at wash station 23 thereby reducing exposure to a contaminant. Subsequent additions to first container 1 may occur in similar fashion, as desired. After all desired additions to first container 1 have been completed, first container 1 contents may be is aspirated or otherwise removed from first container 1 and dispensed or transferred to desired locations where other functions, such as genetic sequencing, a pharmacogenetic test and the like, can be performed. Then, the tip 28 may be removed from pipettor 12 or 19 and disposed to tip 28 waste 24, thereby reducing exposure to a contaminant. By using a single tip 28 for multiple reagent and singular sample or prepared sample manipulations can reduce solid waste and can provide reduced cost while maintaining desired levels of contamination reduction. Similar steps may be performed with the pipettors 12 or 19 even if they do not include a tip 28.

Figure 14:
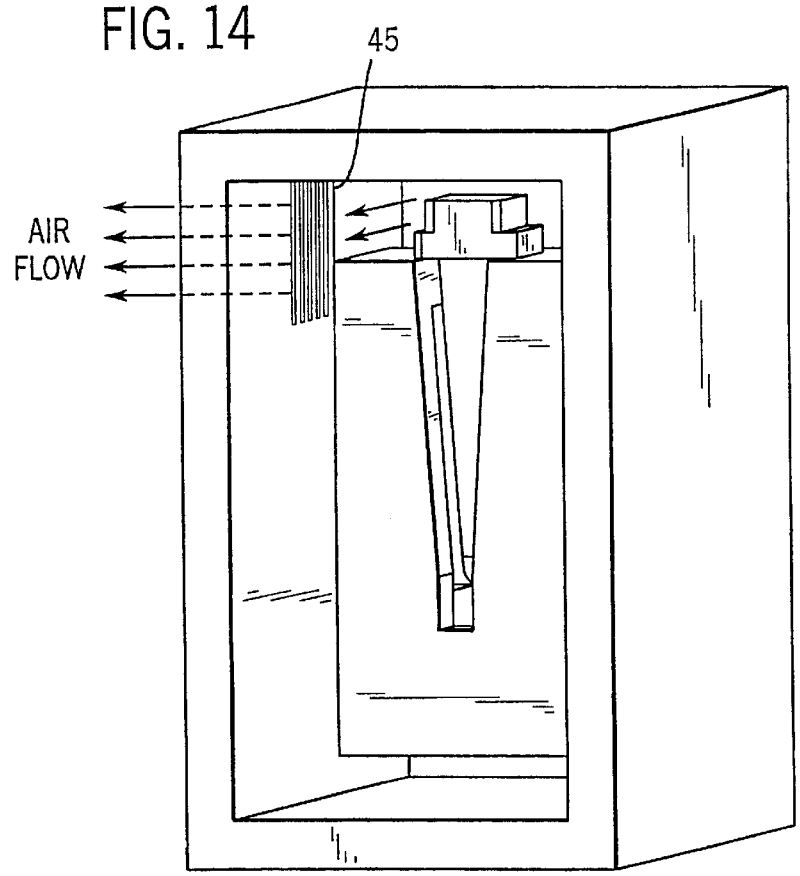
FIG. 14 shows a port provided in operative relationship with the process path of FIGS. 3A and 3B.

Mixing with mixer 5 or other motions imparted to first container 1 may induce unintended distribution, e.g. aerosoling, of fluids contained in first container 1. FIG. 14 shows feature or port 45 integrated into first process path 11 at appropriate locations. Port 45 is fluidly connected with a fluid pressure source, such as a negative fluid pressure source like a vacuum and the like, that draws air flow above first container 1 away from adjacent containers 1 on first process path 11 to a more desirable location. In this method, undesirable airborne contaminants may be routed to controlled locations.

Washing of microparticles used in some methods performed by the structures 1a and 1b, viz. immunodiagnostic and/or PCR sample preparation methods, may utilize removal, evacuation or pipetting of unbound or bound microparticles from first container 1 and/or other constituents of the first container 1 contents, such as if some of the first container 1 contents were attracted to and held by magnet 4.

Figure 15:
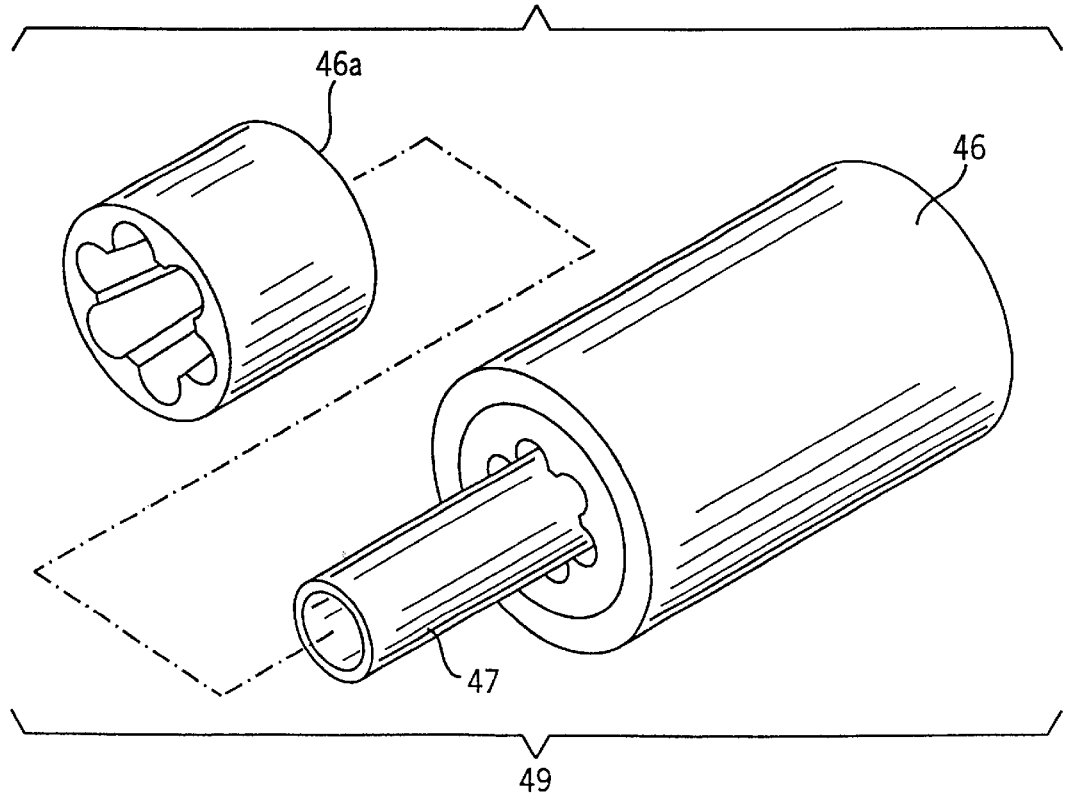
FIG. 15 is an exploded perspective view of a pipettor for use with the structure of FIGS. 3A and 3B.
Figure 16:
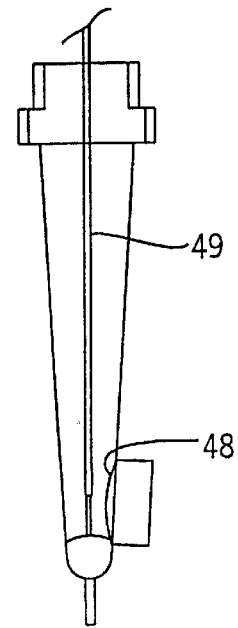
FIG. 16 illustrates one operation of the pipettor of FIG. 15.

To perform this washing, at least one wash zone 50 is located at an appropriate position along first process path 11. Within a wash zone 50 resides a probe 49, shown in FIG. 16, constructed to automatically evacuate or pipette first container 1 contents, such as unbound or bound microparticles from first container 1. More than one probe 49, such as 4, may comprise a single wash zone 50. Washing steps, e.g. magnetic separation, aspiration, dispense, are further described in the '784 patent.

Where contamination is a concern, such as with DNA/RNA determinations, probe 49 can be formed with an outer tube 46 and inner tube 47 as shown in FIG. 15. Outer tube 46 may be held substantially concentrically with respect to inner probe 47 via member 46a. In some embodiments, the member 46a may function as a fluid conveying conduit. In one embodiment, outer tube 46 is fluidly connected to a wash fluid source and inner tube 47 is fluidly connected to a vacuum source routed to waste. The wash fluid may be used for many purposes, such as to chemically wash unbound particles from particles bound to an item of interest held in first container 1, and also to remove undesirable items, i.e. contamination, from inner tube 47 after inner tube 47 comes into contact with fluid, such as fluid in the first container 1, during evacuation.

To improve methods of attracting microparticles to walls of first container 1, the microparticles within the first container 1 may be exposed to a magnet station comprising two magnets disposed adjacent to the first container 1 along opposite sides of the first container 1.

Figure 17:
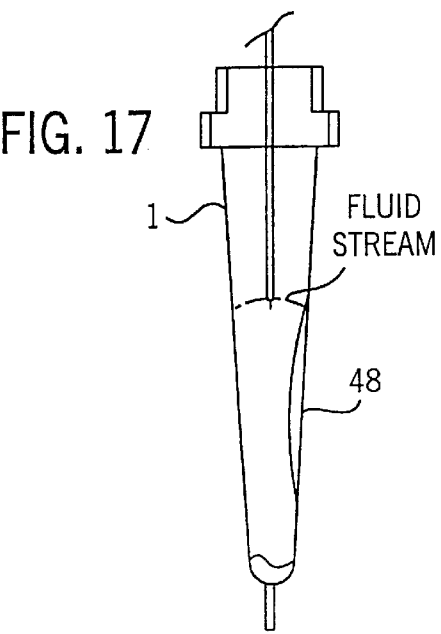
FIG. 17 illustrates another operation of the pipettor of FIG. 15.

Microparticles attracted to side wall(s) of first container 1 can be resuspended at any time, such as during washing, via a suitable device, such as mixer 5 shown in FIG. 13. Alternately, a probe 3 or 49 can be used to effect fluid and/or solid resuspension within the first container 1 by appropriate movement of fluid within the first container 1. In such an embodiment, fluid, such as wash solution, is dispensed from a probe 3 or 49 such that a single or plurality of fluid streams is directed at a position within the first container 1, such as a vertical wall thereof, where relevant fluid and/or solid material to be resuspended is expected to reside. In this manner, the material to be resuspended in the first container 1 may be dispersed within the first container 1 as shown in FIG. 17.

After processing of first container 1 contents is complete according to the selected format or protocol, the first container 1 contents is moved from first container 1 and placed into second container 15 shown in FIG. 3. Material, such as reagent, additions to second container 15 occurs via pipettor 12. Second container 15 is then sealed with sealer 21.

Where relatively quick heating and cooling rates of the second container 15 are desired, the second container 15 can be constructed to sustain relatively quick thermal energy transfer rates by using a relatively large heated surface to second container 15 contents volume ratio and/or a relatively thin wall(s) of the second container 15.

To facilitate transfer of first container 1 contents to second container 15 in an automation fashion, second container 15 can be constructed with a first chamber and a second chamber with a first chamber opening being relatively larger than a second chamber opening. Pipettor 12 can enter and can fill the first chamber with first container 1 contents and other reagents. Then, the first chamber opening may be sealed with sealer 21. The relatively smaller second chamber opening may restrict the contents of the first chamber from moving to the second chamber. Alternatively, the first chamber opening may be sealed by sealer 21 to a first level called a "soft-seal" prior to transfer of the container to spinner 22. In this case, after removal of the second container 15 from spinner 22, the first chamber opening may be sealed by sealer 21 to a second level different than the first level.

Second container 15 is transported to a spinner device 22 that moves the second container 15 such that contents of the first chamber are displaced to the second chamber by centrifugal force. After the contents of the first chamber have moved to the second chamber, second container 15 is removed from spinner device 22 to a heat transfer device for further processing. Alternately, filling of second container 15 to its second chamber can be achieved by force induced by pressure from fluidics coupled to pipettor 12, or, pipettor 12 can enter the second chamber of second container 15 and thereby fill the second chamber.

Although capillary tube or tubes having capillary like construction are amenable to desirable heat transfer rates, filling such tubes typically involves force or centrifugation to move liquid into the tube. In another embodiment, second container 15 comprising assembly 15c, illustrated in FIGS. 27A through 27F, may be used. In this embodiment, second container 15 is accepts contents through opening 57. The orifice of opening 57 of second container 15 is relatively larger than a capillary tube to allow for automated pipetting of contents into second container 15 without any secondary operations, such as centrifugation. Prior to further DNA amplification, second container 15 may be sealed to reduce contamination. Seal 15b engages second container 15 to provide contamination reduction and evaporation control. An outer wall 58 of seal 15b is relatively smaller than an inner wall 59 of second container 15 such that, when engaged with second container 15, contents in second container 15 can displace around outer wall 58. This displacement of contents increases heat transfer to liquid area ratio thereby providing for relatively rapid heat transfer. In some embodiments, outer wall 58 can include fins (not shown) such that the fins engage second container 15 inner wall 59 to position seal 15b substantially concentrically with respect to second container 15 thereby providing for substantially uniform displacement of contents around the outer wall 58 of seal 15b and for substantially uniform heat transfer to the contents.

Figure 27A:
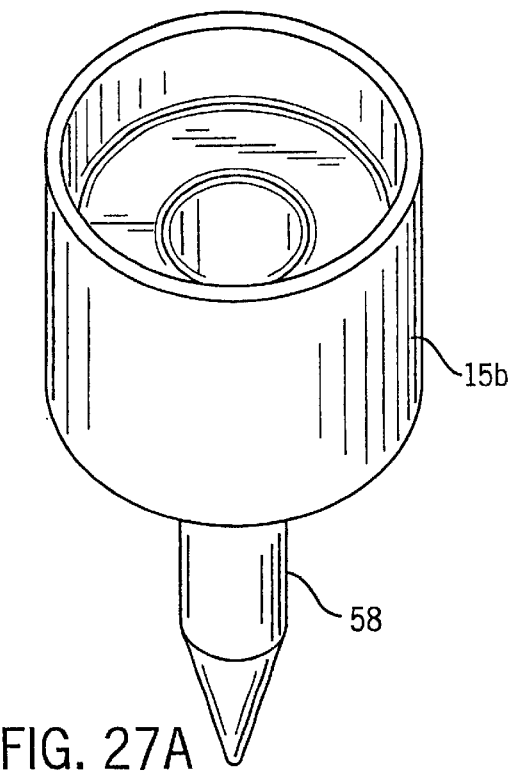
FIGS. 27A through 27F are perspective views of a container and seal for use with the structure of FIGS. 3A and 3B.
Figure 27B:
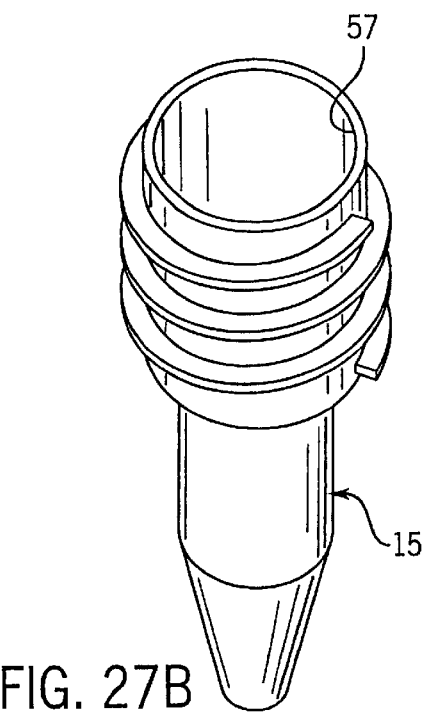
Figure 27C:
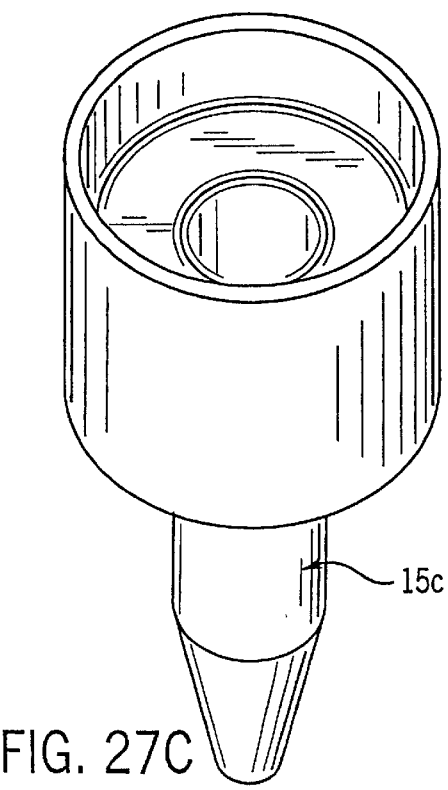
Figure 27D:
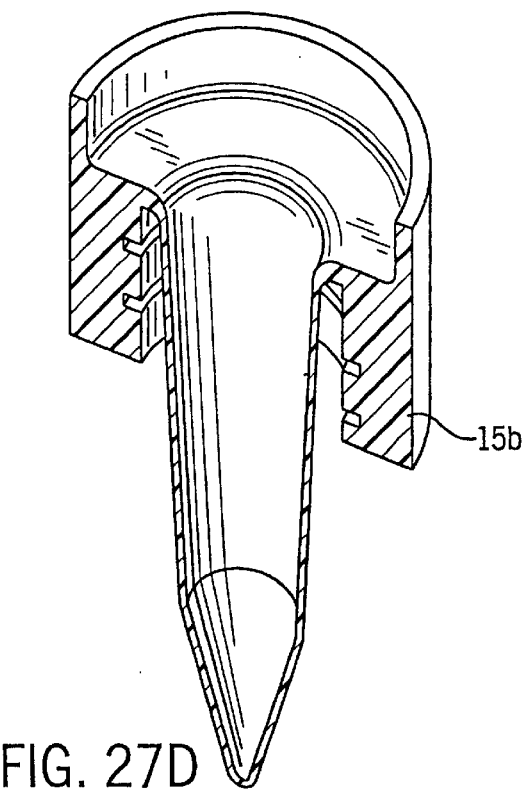
Figure 27E:
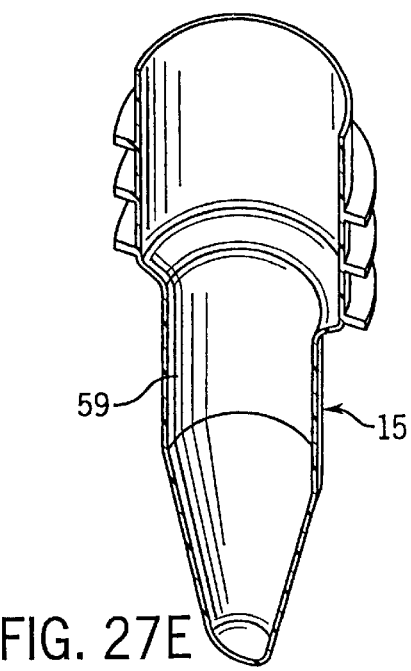
Figure 27F:
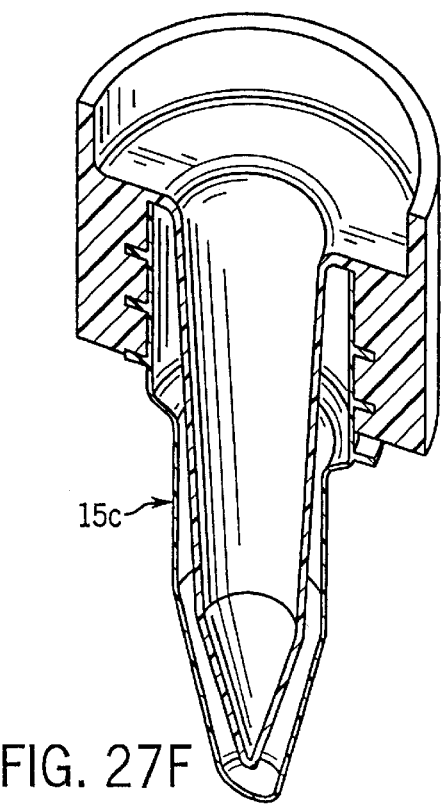

Second container 15 and seal 15b are matable to form assembly 15c shown in FIGS. 27C and 27F. This assembly 15c can be transferred to a second process path or thermal cycling/detection module 16 for further processing.

In one embodiment, the steps of transporting the second container 15 to the spinner device 22 occur after pipettor 12 adds up to three reagents and sample to second container 15. A robot then moves second container 15 to a second process path or heat transfer/detection apparatus 16. The apparatus 16 may bring the second container 15 to a temperature the same as or different from a temperature(s) to which the first process path brings the first container 1.

Figure 3A:
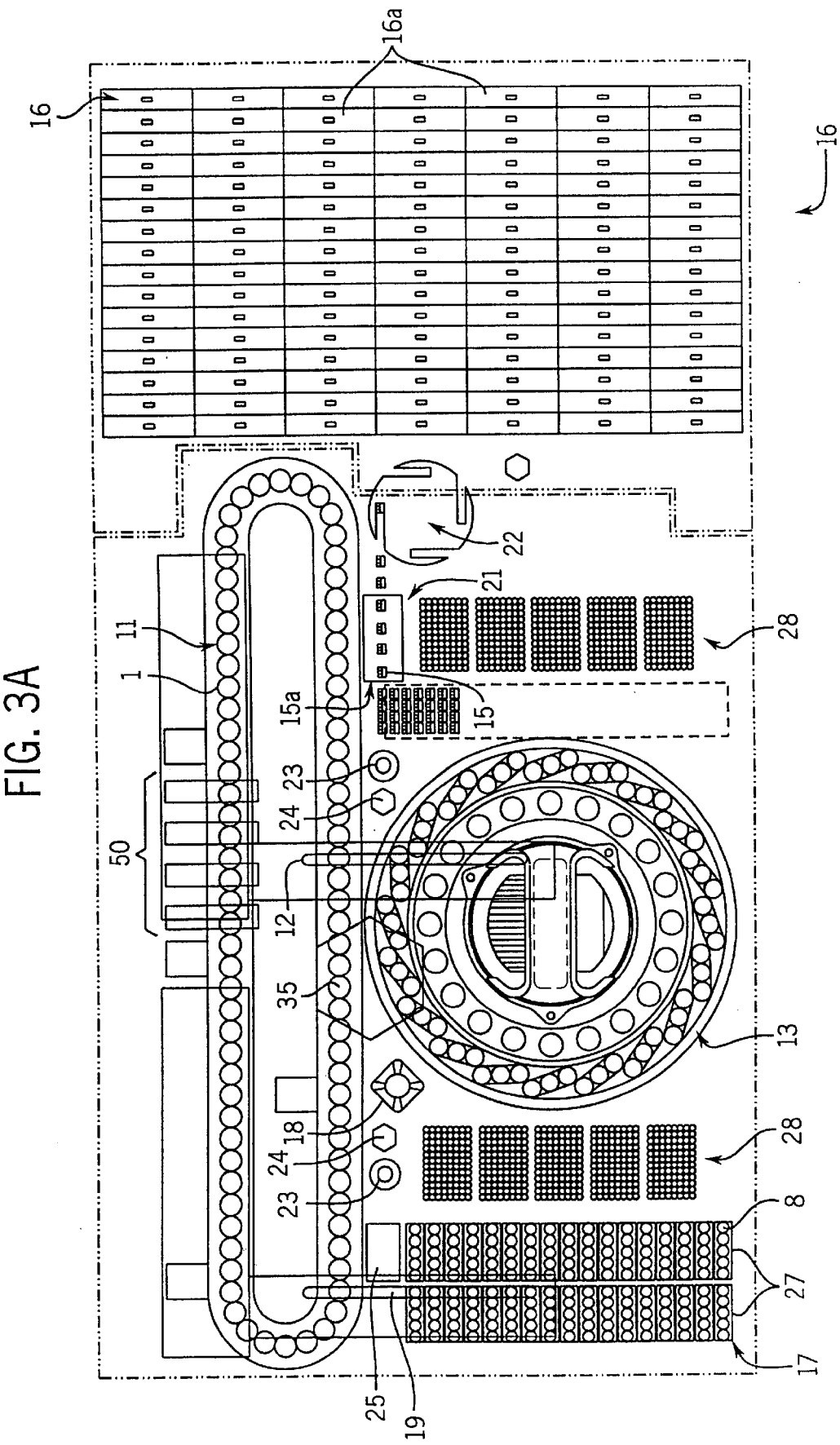
FIG. 3A is a generic top view of another structure described herein.
Figure 3B:
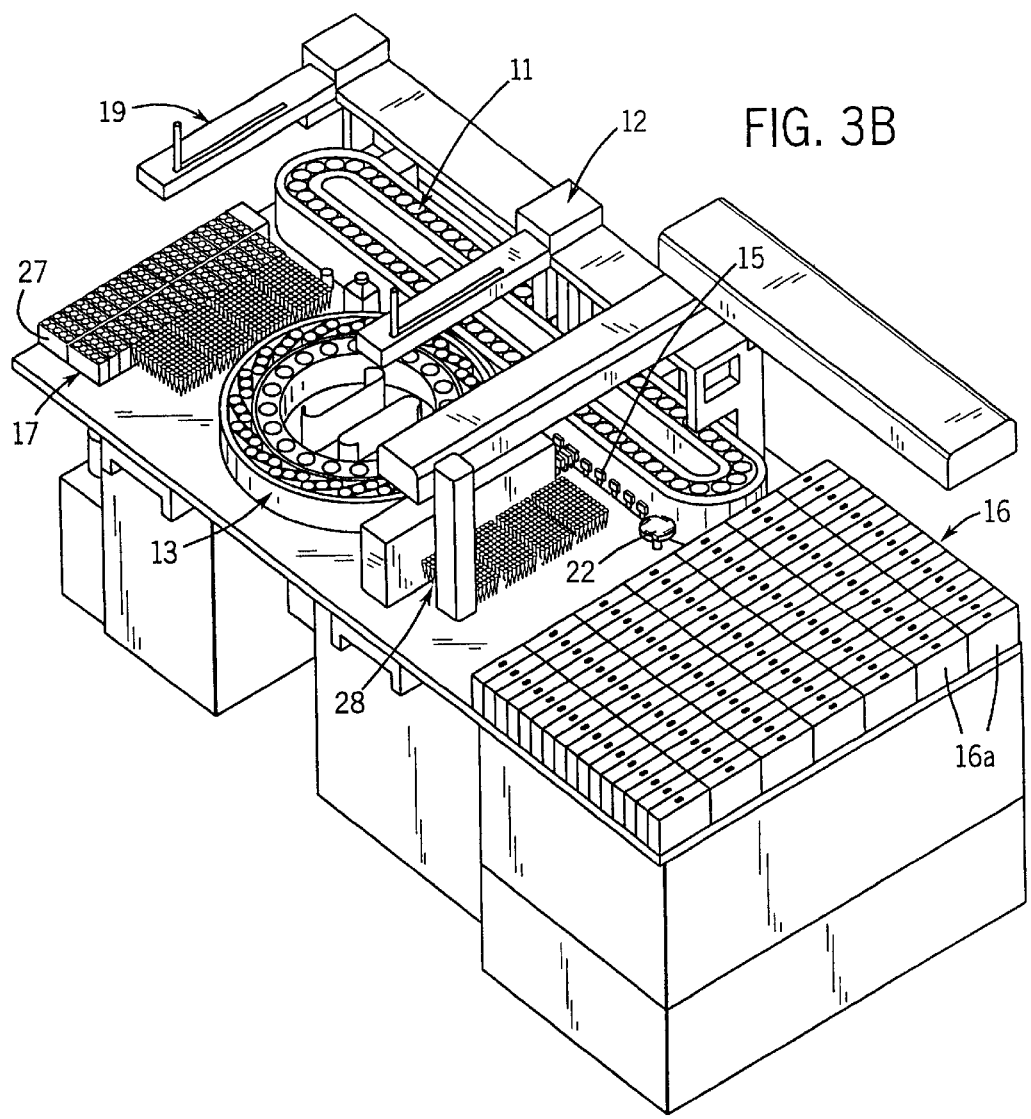
FIG. 3B is a perspective view of the structure shown in FIG. 3A.
Figure 4:
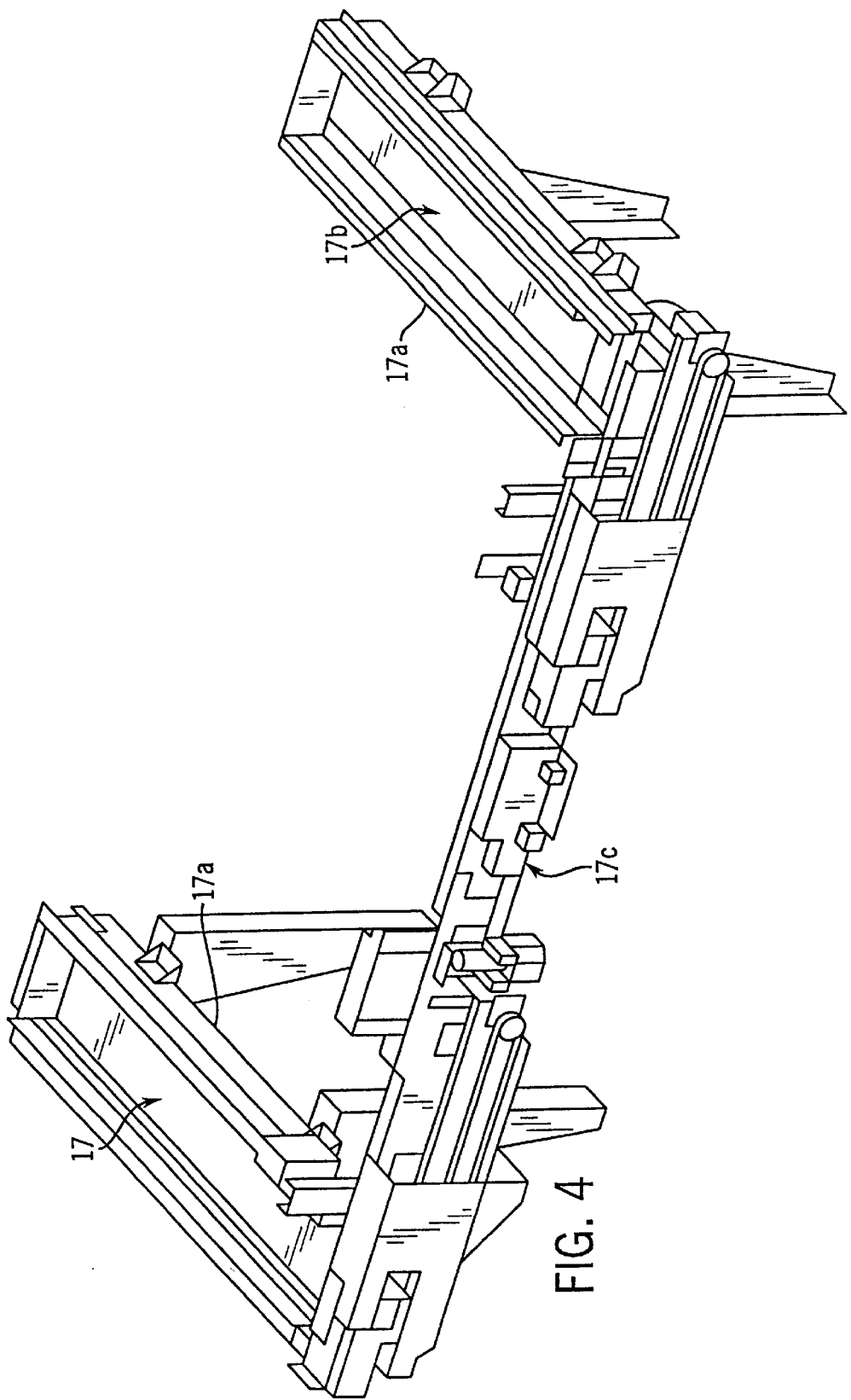
FIG. 4 is a perspective view of a sample queue for use with the structure of FIGS. 3A and 3B.

FIGS. 3A and 3B illustrate one construction of the heat transfer/detection apparatus 16 comprising 112 heat transfer/detection modules 16a such that throughput of samples prepared on first process path 11 is compatible with PCR processing times of approximately one hour to yield a structure throughput of approximately 100 tests per hour. Heat transfer/detection apparatus 16 can be used for isothermal reactions, thermal cycling, integrated heat transfer and detection, among other processes. In some embodiments, heat transfer functions and the detection functions can be performed by separate structures, e.g. the apparatus 16 can comprise a hat transfer structure and a detection structure, which may be located adjacently, separately or in any appropriate fashion. After detection in apparatus 16, second container 15 is automatically removed and discarded to waste by the robot or transferred to another detector for further determinations.

In the embodiment shown in FIGS. 3A and 3B, isolated sample preparation can be performed on first process path 11 and amplification and detection can be performed on the adjacent apparatus 16. Here, these two processes are substantially separated such that contamination concerns specific to DNA/RNA chemistries may be reduced.

The first process path 11 for automated preparation of sample may be operatively connected to the apparatus 16 for amplification and detection by further apparatus such as the robot.

In some embodiments, the second process path 16 is a continuation of the first process path 11 thereby forming a single process path. In such an embodiment, any of the containers described herein may be used along the entire process path thereby eliminating the need to transfer from container 1 to container 15. In other words, sample can be transferred from the sample container 8 to a single process container that is used to perform all the steps described herein.

There are a number of other possible modifications to the structures 1a and 1b. In one modification, first process path 11 in FIGS. 3A and 3B can include a process step performance lane, such as first process path 11, where a process step is selectively automatically performed, and a process step avoidance lane where the process step is selectively automatically avoided, possibly located to avoid a wash zone 50. First container 1 containing the reaction mixture may be selectively automatically positioned in a selected one of the process step performance lane or the process step avoidance lane based on selected format or protocol similar to the manner described in the '784 patent.

In other modifications, second container 15 could be a capillary tube, a tube possessing capillary tube characteristics, a reaction vessel described in U.S. Pat. No. Des. 401,700, a reaction tube, such as that supplied by Cepheid of Sunnyvale, Calif., a tube similar to first container 1, and the like. Heat transfer/detection apparatus 16 could utilize Peltier, microwave, resistive, forced air and/or liquid heating/cooling technologies. Modules 16a could also utilize Peltier, IR, microwave, resistive, forced air and/or liquid heating/cooling technologies, and may be substantially similar to the thermal cycler and/or detector components of the Smart Cycler™ system supplied by Cepheid (Sunnyvale, Calif.), the Tetrad™ or PTC-100™ systems supplied by MJ Research, INC (Waltham, Mass.), the Sprint™ system supplied by Hybaid (Franklin, Mass.), the Multigene™ system supplied by Labnet International (Woodbridge, N.J.), the RoboCyler™ 40 or 96 systems supplied by Stratagene USA (La Jolla, Calif.), the 480, 9600, or 9700 systems supplied by Perkin-Elmer (Foster City, Calif.), and the like.

Further modifications of the structures 1a and 1b are possible. The following examples of such modifications utilize common reference characters for similar structures.

Figure 20:
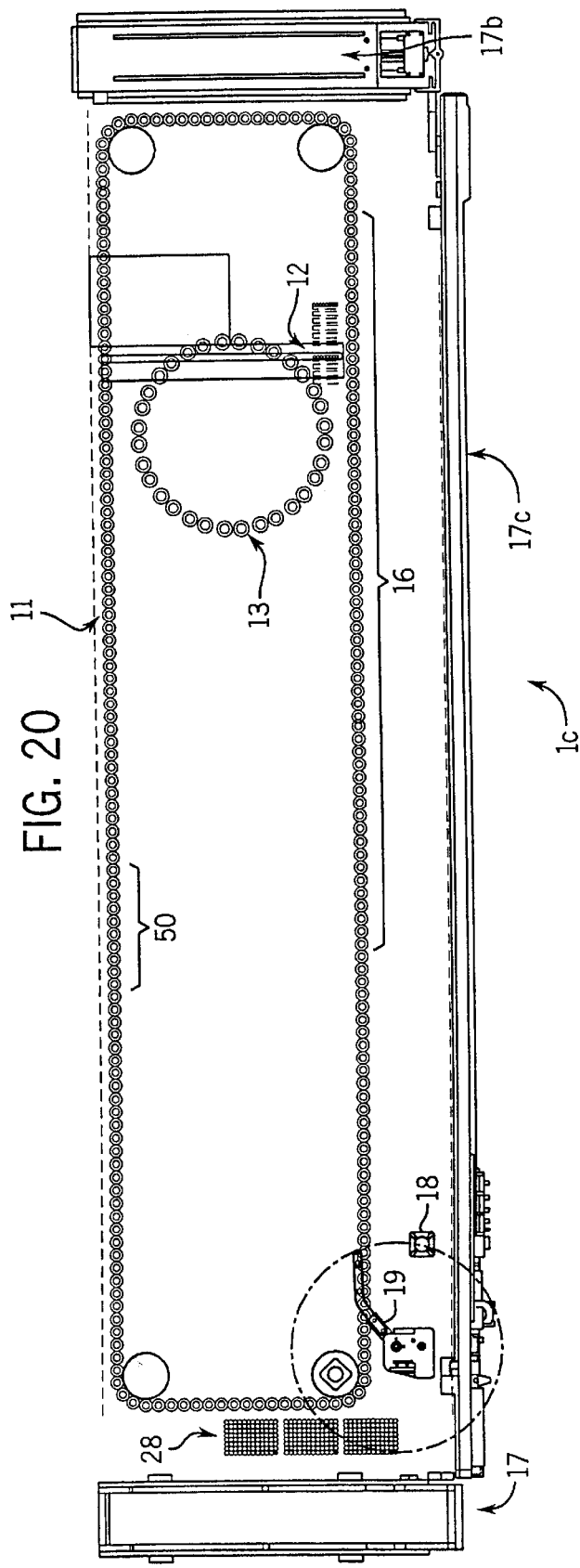
FIG. 20 is a top view of another structure substantially similar to the structure of FIGS. 3A and 3B.

In another structure 1c shown in FIG. 20, heat transfer/detection apparatus 16 can be integrated into first process path 11 as shown in FIG. 20. Here, first container 1 remains on first process path 11 while passing through thermal zones amenable to the desired format.

Figure 21:
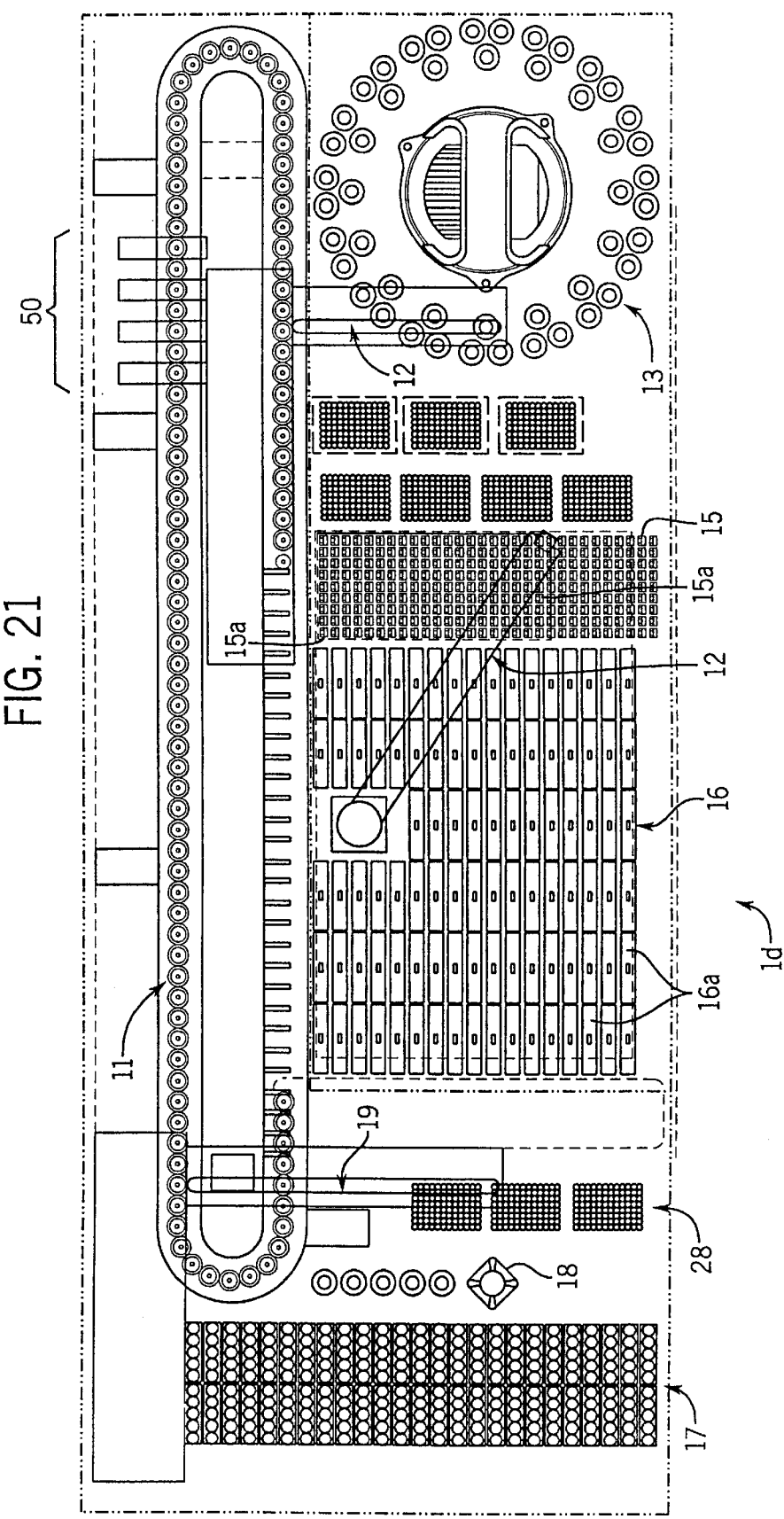
FIG. 21 is a top view of an additional structure substantially similar to the structure of FIG. 20.

In an additional structure id shown in FIG. 21, the first container 1 is transferred to second container 15 and, subsequently, second container 15 passes through thermal zones amenable to desired format. Thus, a portion of a thermal reaction can be implemented in second container 15 processing line 15a prior to transfer of the second container 15 to heat transfer/detection apparatus 16.

Figure 22:
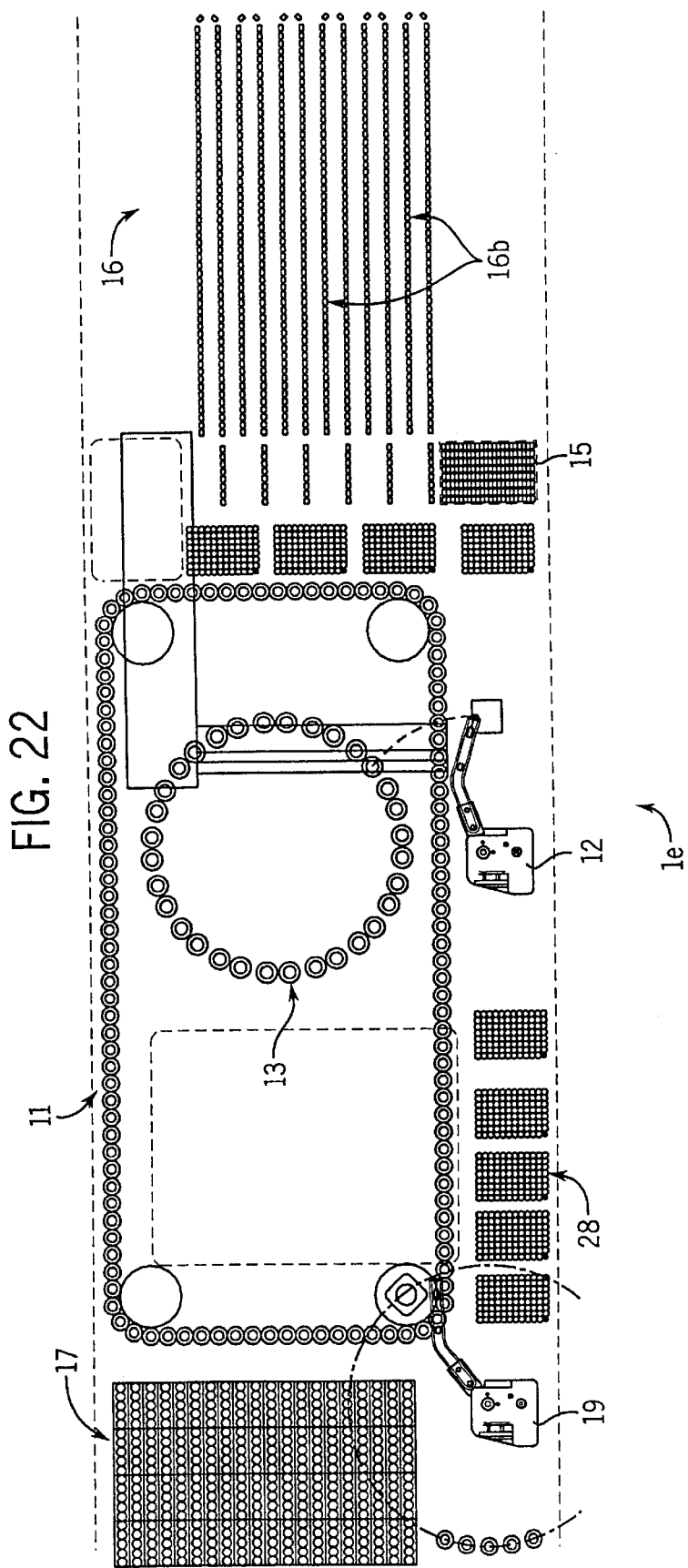
FIG. 22 is a top view of a further structure substantially similar to the structure of FIG. 21.

In another structure 1e illustrated in FIG. 22, the second process path or heat transfer/detection apparatus 16 can include a plurality of individually controlled second process sub-paths or heat transfer/detection paths 16b. Each of the heat transfer/detection paths 16b may be dedicated to a particular item of interest in a manner substantially similar to the construction of the Abbott Prism® instrument.

Figure 23:
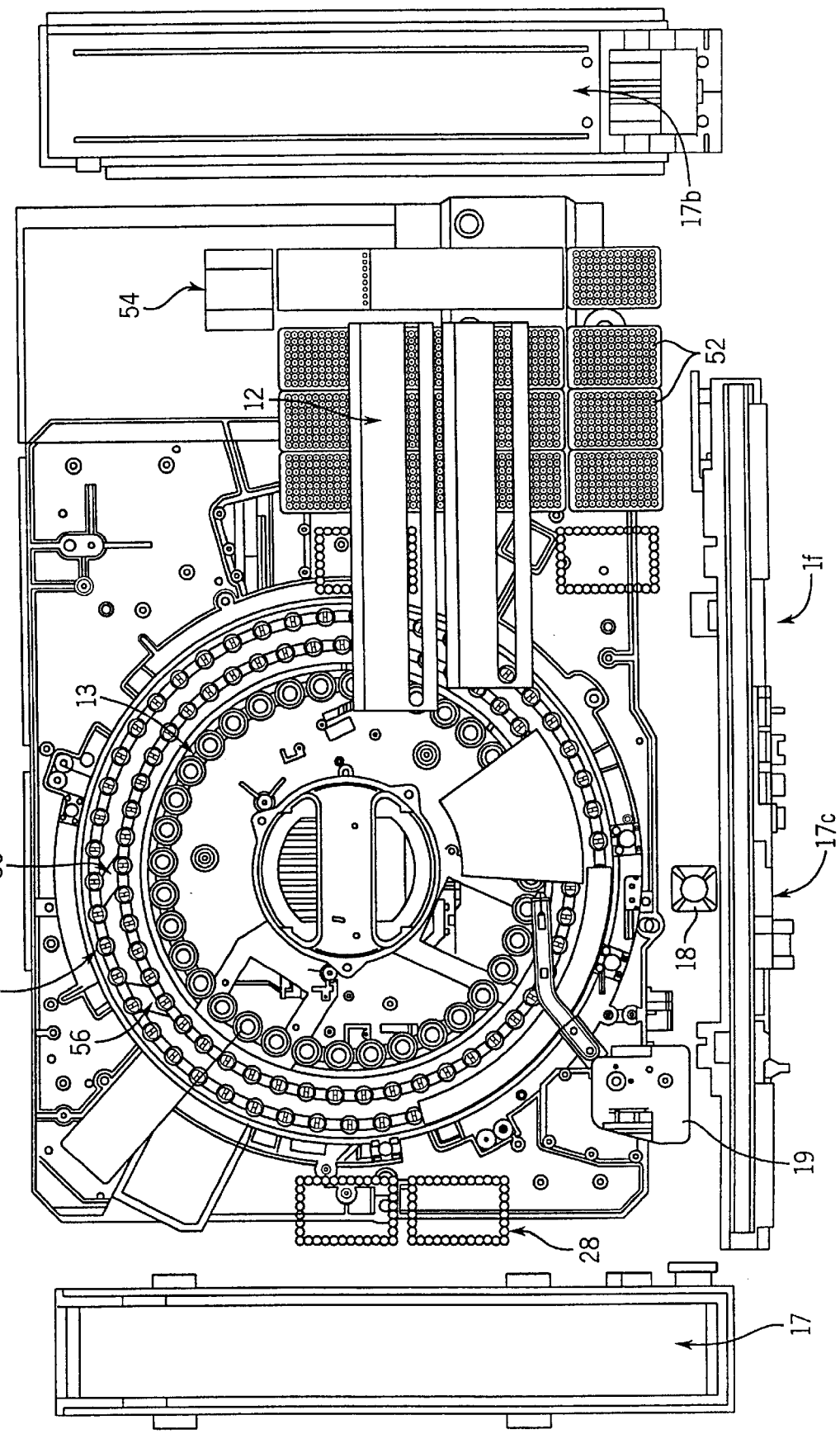
FIG. 23 is a top view of another structure substantially similar to the structure of FIG. 22.

In an additional structure 1f depicted in FIG. 23, first container 1 contents processing can be preformed and the processed first container 1 contents transferred into a reaction vessel or tray 52, such as a multiple well (e.g. 96 wells) tray filled with desired reagents. The structure 1f may also include a bypass region 56 on the first process path 11, as described in the '784 patent. The tray may be sealed and moved to an output queue 54 for transfer, either manual or automatic, to further apparatus such as heat transfer/detection apparatus 16. In this modification, further methods may be employed to improve customer lab workflow by sorting samples by desired assay in a sample handling queue 17 prior to further processing. This allows for consolidation of heating and cooling devices, such as the number of modules 16a within the heat transfer/detection apparatus 16, needed to process chemistry requiring different heating and cooling protocols for each assay.

The structures described herein and their use may be optimized, for example, the structures may be adjusted such that number of determinations in a given time period are increased, by allocating items such as determinations to be performed, samples, reagents, containers, etc., across elements of the structure(s).

For example, an operator loads samples on the sample handler 17 of the structure in any order. To reduce cost per determination or to improve structure reliability, among other things, the number of items present in a structure may be reduced. Some determinations, for example DNA/RNA amplification and detection, require heating and cooling protocols that may vary from determination to determination. This may complicate cost and/or item reduction. To achieve these reductions, items may be allocated across elements of the structure(s).

In the embodiments discussed herein, a determination method may consist of a number, such as three, of processes. In one employment, a determination comprises a first process, a second process and a third process. The first process may be common to all determinations, such as DNA/RNA sample preparation, sample incubation, immunodiagnostic sample preparation and determination and the like. The second process, for example, amplification and the like, may be specific to a given determination. The third process, for example, detection, may be either common to all determinations or specific to a given determination.

To allocate items across elements of the structure(s), samples are identified and then grouped by commonality in second and third processes. For example, one DNA/RNA assay may be processed according to one protocol, such as Protocol A described below, in one module 16a, 16b, 16c or 16d while another DNA/RNA assay may be processed according to another protocol, such as Protocol B described below, in another module 16a, 16b, 16c or 16d. By supplying samples, selected by common second and third processes, from sample handler 17 to process path 11, allocation of modules 16a, 16b, 16c or 16d to specific determination(s) may be achieved while reducing the number of modules 16a, 16b, 16c or 16d and containers 52 needed, while increasing throughput.

Sample sorting may comprise identifying sample information by reading a bar code on container 8 held by the sample handler 17 with a barcode reader. The containers 8 may then be sorted (mechanically) with other containers 8 within a given carrier 27 and then carriers 27 may then be sorted with other carriers 27 in the sample handler 17 by determinations having common second and third processes. After sorting, samples from containers 8 are transferred to container 1 by pipettor 19. Alternately, sample sorting may be achieved by pipettor 19 selectively transferring sample from container 8 to container 1 on process path 11 based on predetermined, sorted order.

Once the sample is in the container 1 on the process path 11, the first process comprising the determination method is performed. After the first process is finished, depending on the particular structure used, the second and/or third processes may occur in either the process path 11, in one or more modules 16a, 16b, 16c or 16d, or in separate apparatus.

By sorting or grouping samples according to common second and/or third process, an optimal number of modules 16a, 16b, 16c or 16d can be allocated to determining a given item of interest, viz. the greatest number of determinations of a given item of interest can be discerned, associated samples can be suitably sorted, and elements or items of or in the structure(s), such as containers, reagents and the like, can be appropriately duplicated over two or more modules 16*a*, 16*b*, 16*c* or 16*d* on a given structure(s). Similarly, two or more modules 16*a*, 16*b*, 16*c* or 16*d* can be duplicated based on specific determination protocols.

Figure 24:
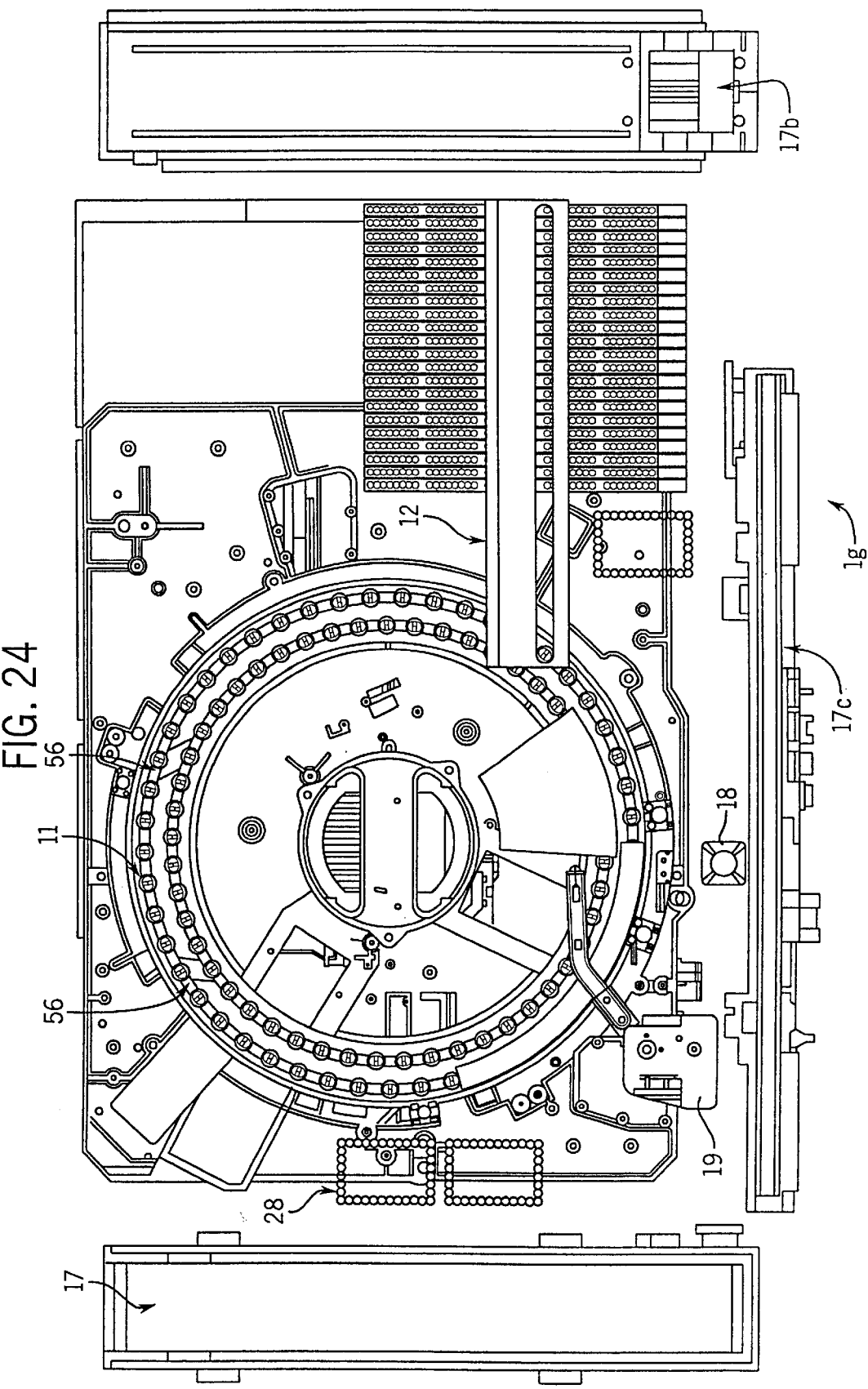
FIG. 24 is a top view of yet a further structure substantially similar to the structure of FIG. 23.

FIG. 22 shows another structure 1*e* where modules 16*b* can be duplicated according to sample sorting outcomes. FIGS. 23 and 24 show other structures 1*f* and 1*g* where modules 16 can be located exterior to the structure(s). Here, sorted samples can be duplicated across multiple modules 16 exterior to the structure(s) 1*f* and 1*g*.

FIG. 20 shows another structure 1*c* where module 16 is integrated into process path 11. Sample sorting here allows for process path 11 to be programmed for one determination for a first period of time and then be programmed for another determination for a second period of time.

Figure 26:
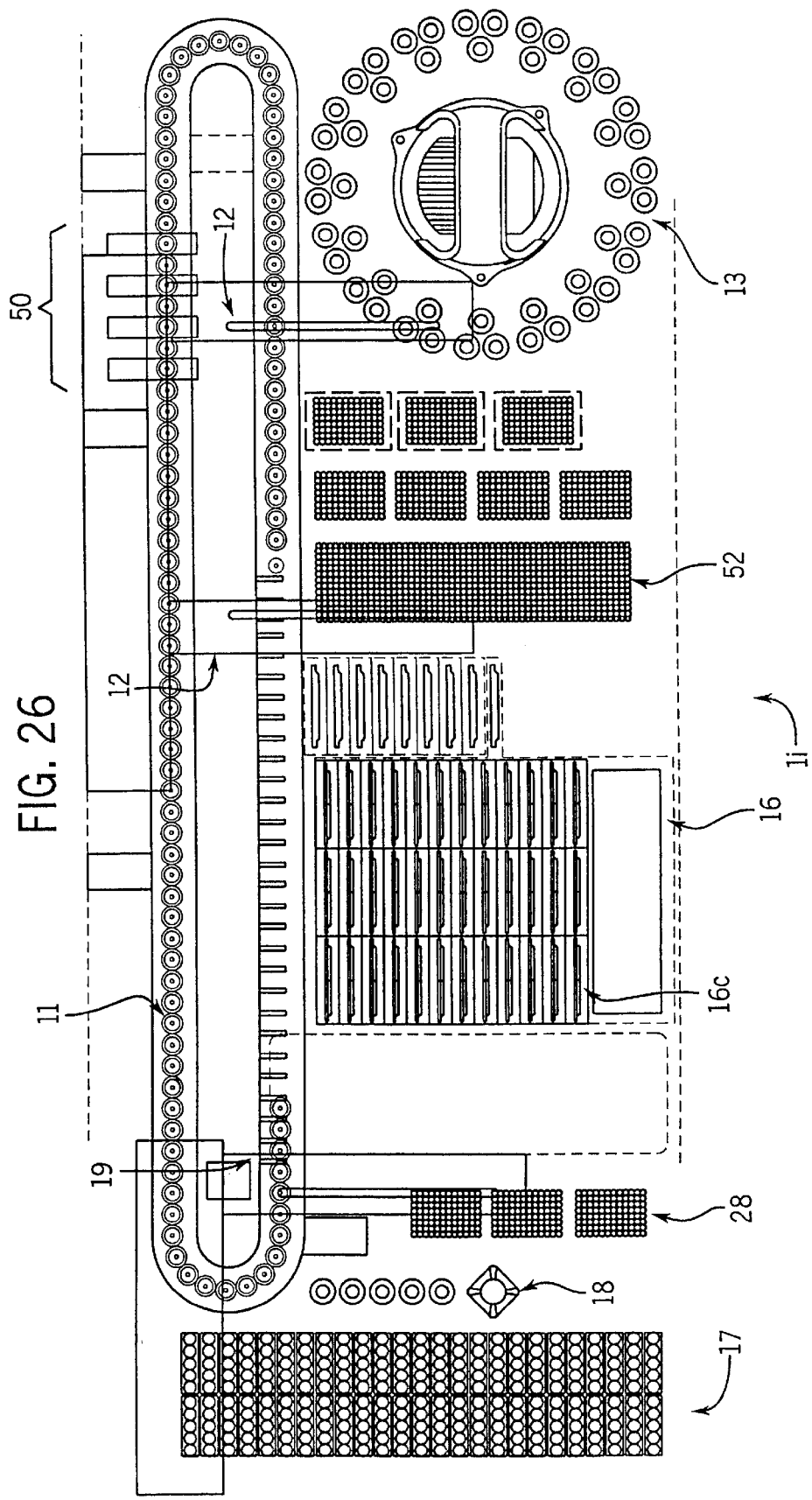
FIG. 26 is a top view of yet a further structure similar to the structure of FIGS. 3A and 3B.

In applications involving sorting samples by determination in sample handling queue 17 prior to further processing, it may be desirable to form relatively small groupings. The grouping size can determine the size of tray 52 and its corresponding heat transfer/detection apparatus 16. In a structure 1*i* depicted in FIG. 26, samples may be sorted by determination into relatively small groupings including about twelve samples. The tray 52 and thermal cycling/detection module 16*c* within thermal cycling/detection module 16 are both configured to accommodate groupings of twelve with module 16*c* providing individual control of each grouping of twelve. The structure 1*i* may reduce the number of thermal cycling/detection modules 16*c* required to maintain desired throughput.

Additional enhancements, such as with software controlling the structure, can be provided to manage test distribution lists, to generate reagent load maps, to make reagent loading suggestions, and to manage data.

In an further structure 1*g* shown in FIG. 24, first container 1 contents preparation can be preformed and the prepared first container 1 contents can be transferred into another container or tray. The container is moved to an output queue for manual or automatic transfer to further apparatus that performs reagent addition, heat transfer, and detection.

Figure 25:
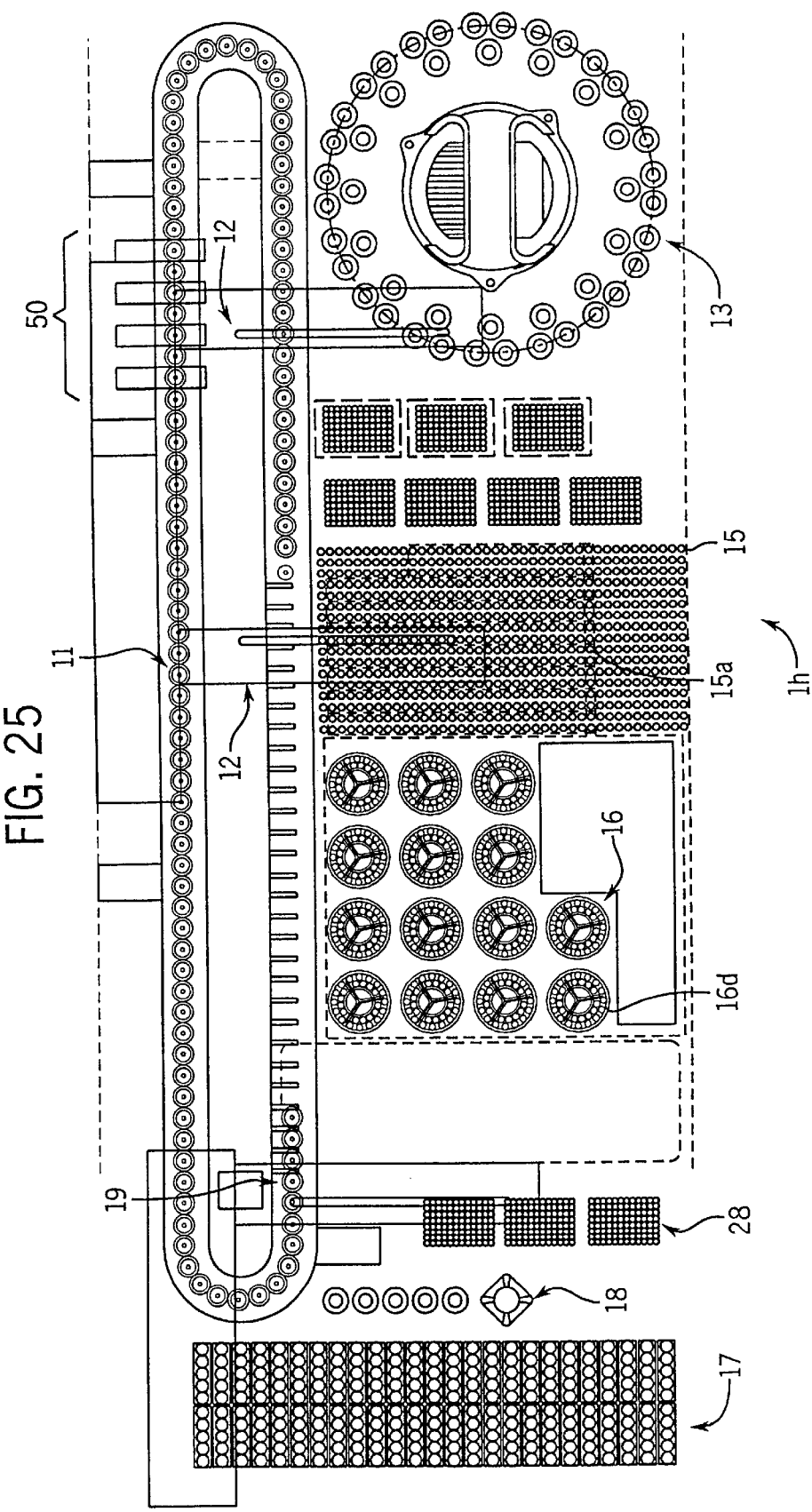
FIG. 25 is a top view of yet a further structure similar to the structure of FIGS. 3A and 3B.

In an additional structure 1*h* depicted in FIG. 25, samples do not need to be sorted in sample input queue 17, and the number of thermal cycling/detection modules 16*d* required is reduced. In this structure 1*h*, second container 15 is transferred to thermal cycling module 16*d*, each module 16*d* being individually controlled and each having a detector. Module 16*d* may thermally transfer second container 15 through a plurality, such as about two or three, thermal zones within a carousel over a number of positions. One position on the carousel contains a detector. Module 16*d* is designed to accept additional containers 15 sequentially while other containers 15 are being processed within module 16*d*. Alternately, module 16*d* can be fully loaded with containers 15 and all containers can be processed substantially simultaneously.

Other embodiments of the module 16*d* are illustrated in FIGS. 30A, 30B, 31, 32A and 32B. Common reference numbers are used to indicate similar structures in FIGS. 30A, 30B, 31, 32A and 32B. These other embodiments of the module 16*d* can be used for thermal amplification and detection of PCR products, for example.

A tray 70 has at least one compartment or well 71 where thermal amplification can occur. While the embodiments of FIGS. 30B and 32B includes 8 wells 71, the number of wells 71 can be modified as desired. The well 71 can be numbered and may be bar coded to facilitate identification. In this manner, well 71 position, contents, etc. can be checked by machine, such as with optics. In some embodiments, the tray 70 may be a disposable item easily removed from the associated structure.

A well 71 may be bounded on at least one side by a divider 72 to reduce exposure of contents of a well 71 to a contaminant. To further reduce exposure to a contaminant, the well 71 may be removably covered or sealed.

The tray 70 is operatively connected with a motor 76 (FIG. 31), such as a stepping motor, a servo motor or the like controlled by a microprocessor and the like, by a drive shaft 73 thereby providing for desired, controlled rotation of the tray 70.

Figure 30A:
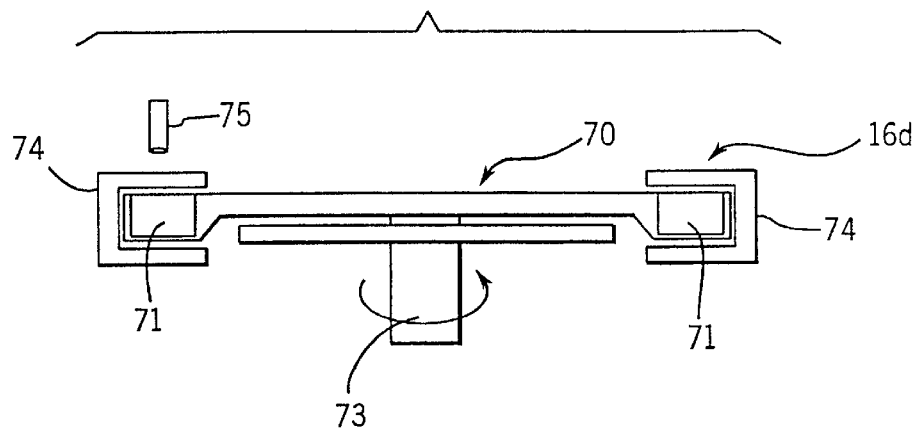
FIG. 30A is a sectional view of a portion of the structures described herein.
Figure 30B:
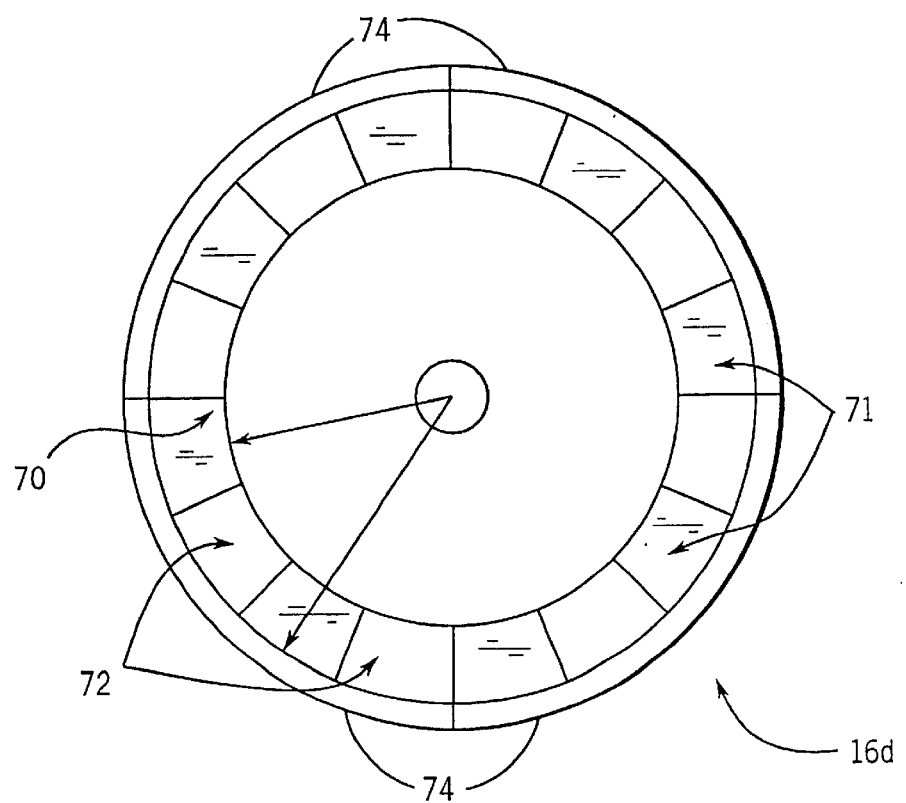
FIG. 30B is a top view of the portion of FIG. 30A.
Figure 31:
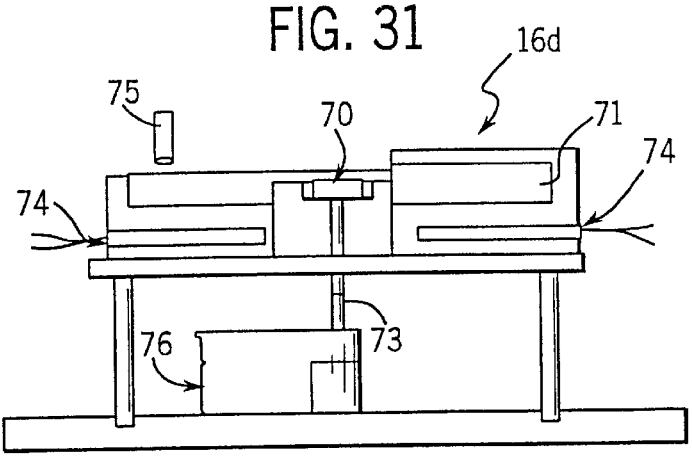
FIG. 31 is a sectional view of a portion of the structures described herein.
Figure 32A:
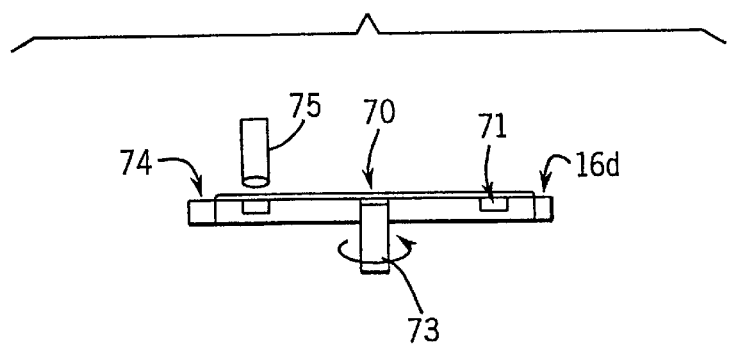
FIG. 32A is a sectional view of a portion of the structures described herein.
Figure 32B:
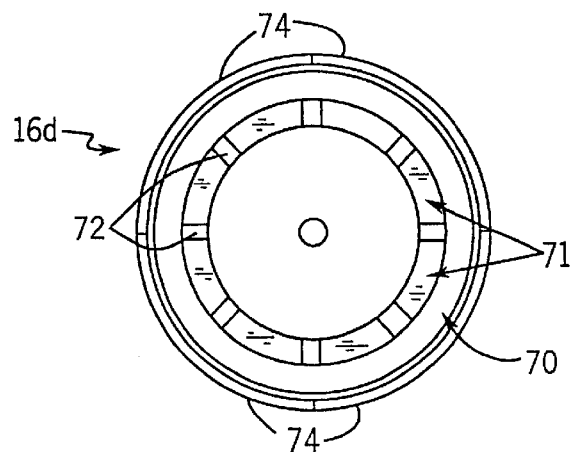
FIG. 32B is a top view of the portion of FIG. 32A.

Container 8 contents can be transferred from the first process path 11 to the well 71 for amplification and detection. To provide desired thermal exposure of the tray 70 and the well 71, at least one heater 74 is thermally associated with the tray 70. If multiple or different thermal exposures are desired, then an appropriate number of heaters 74 can be included. As shown in FIGS. 30B and 32B, four (4) heaters 74 are disposed in thermal association with the tray 70 thereby providing four different temperatures or different thermal exposures. The heater 74 may utilize electric, microwave, Peltier effect, forced air or similar technology.

The heater 74 may operate such that the well 71 is at a desired temperature prior to or after addition of contents to the well 71. In some embodiments, the heater 74 may be separated from the tray 70 such that the tray 70 is operatively connected with the heater 74 either prior to or after addition of contents to the well 71 on the tray 70.

As the tray 70 rotates, the well 71 and its contents are exposed or brought to the temperature provided by the adjacent heater 74. As thermal variations may be cyclical, i.e. repetitive of a given pattern, rotation of the tray 70 can bring the well 71 and its contents to desired temperature(s) in desired sequence for a desired time period. Thus, the well 71 and its contents can experience consecutive, well-defined temperature zones as the tray 70 rotates. Each heater 74 may correspond to temperatures specific to a given reaction, such as melt, annealing, extension, etc., defined by the particular determination being performed.

A time period during which a given well 71 is located adjacent a given heater 74 is determined by the rotational speed of the tray 70. In some utilizations, a number of rotations or step-wise movements of the tray 70 may be proportional to a number of cycles performed by a currently available thermal cycler. Rotational speed of the tray 70 may be controlled such that the well 71 is positioned adjacent a heater 74 for a specified length of time. For example, a first heater 74 may bring the well 71 to a temperature capable of dissociating, or melting, double stranded DNA strands. A second heater 74, adjacent the first heater 74, may bring the well 71 to a temperature that induces association of complementary strands, such as a target and a primer, or a target and a probe. The second heater 74 or another heater 74 may be used to allow enzymatic polymerase elongation of the primer, and the well 71 is positioned adjacent that heater 74 for a time sufficient for the reaction to finish. By adjusting tray 70 rotational speed, thermal "area," i.e. the area in which the heater 74 can bring the well 71 and its contents to a temperature associated with the heater 74, of the heater 74 and temperature values associated with the heater 74, optimal thermal cycling parameters for a certain assay may be accomplished.

Once the desired thermal exposure of the well 71 is complete, the item of interest present in the well 71 can be detected by detector 75. If the well 71 were sealed, then the seal may be removed or, alternatively, the seal may be made of a material that allows optical transmission so that detector 75 can monitor the well 71 and detect the item of interest, if present. The detector 75 may also read a bar code associated with the tray 70 or the well 71.

The detector 75 may be used in a dynamic (real time) mode, such as to detect, in real time, PCR products by reading the well 71 as it moves with respect to the detector 75. In some embodiments, the detector 75 may read the well 71 every n times the well 71 encounters the detector 75. The number n may be determined to allow for comparing status of the well 71 with a predetermined threshold at a predetermined time(s). The detector 75 can be used for static, end point reads.

The detector 75 may be stationary with respect to the tray 70 or may move with respect to the tray 70. If multiple trays 70 are present, then multiple detectors 75, such as one detector 75 for each tray 70, may be used. Fiber optics may be used to channel light from a well 71 to the detector 75.

The detector 75 may use a light source to illuminate contents of a well 71 at a single or multiple wavelengths, thereby accommodating multiplex detector 75 data reduction of multiple wavelength emission intensity at discrete wavelengths, for example. In some embodiments, the detector 75 may provide single or parallel detection of single or multiple wavelengths, such as fluorescence emissions from the well 71.

Figure 33:
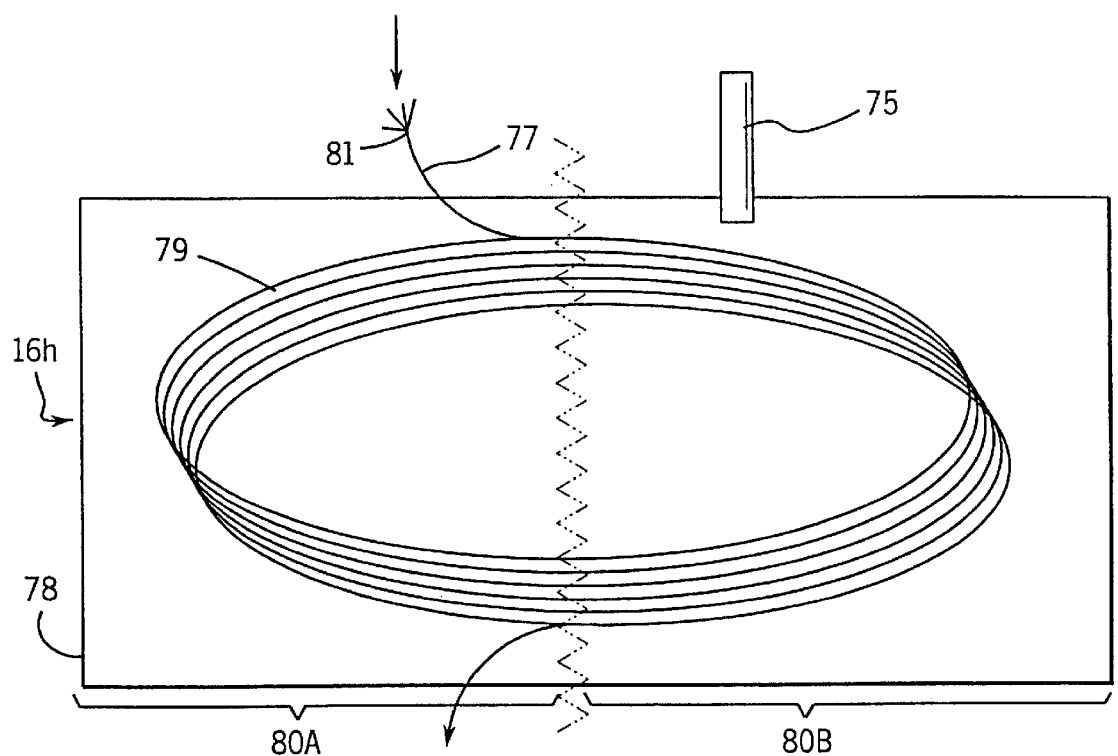
FIG. 33 is a generic plan view of a portion of the structures described herein.

Another module 16h is shown in FIG. 33. This module 16h includes a fluid conveying conduit 77 disposed within a block 78. The conduit 77 may be formed as a coil 79 in the block 78. The block 78 is constructed with suitable thermal energy conductive elements to form at least a first thermal zone 80A having a first temperature and a second thermal zone 80B having a second temperature different from the first temperature. With this construction, some portions of the coil 79 are in a thermal zone 80A or 80B different than other portions of the coil 79 while some portions of the coil 79 are in the same thermal zone 80A or 80B.

Container 1, 8 or 15 contents or fluid can be transferred from the first process path 11 to an inlet 81 of the conduit 77. The fluid forced to flow from the inlet 81 through the coil 79 by suitable means, such as a pump, capillary action, etc. As the fluid flows through the coil 79, the fluid encounters or is brought to different temperatures as it moves between thermal zones 80A and 80B.

The temperatures associated with the thermal zones 80A and 80B can be chosen to match temperatures of specific PCR amplifications. In this embodiment, a number of turns, or loops, comprising the coil 79 is equivalent to the number of cycles performed by a currently available thermal cycler. The fluid flow in the coil 79 is controlled such that the fluid resides in each thermal zone 80A or 80B a specified length of time. For example, one thermal zone 80B may bring the fluid to a temperature capable of dissociating, or melting, double stranded DNA strands. The other thermal zone 80A may bring the fluid top a temperature inducing association of complementary strands, such as a target and a primer, or a target and a probe. This same thermal zone 80A may be used to allow enzymatic polymerase elongation of the primer. Of course, the fluid flow is adjusted to expose the fluid to a thermal zone 80A or 80B for a time period sufficient for the reaction to finish. A detector 75 is disposed adjacent the coil 79 to monitor status of the fluid within the coil 79 in a manner substantially similar to that described above.

Fluid corresponding to various samples may be introduced to the conduit 77 separated by suitable other fluid, such as air, a buffer and the like.

Any heat transfer/detection module can be used in apparatus 16. For example, apparatus 16 can use methods described in U.S. Pat. No. 5,576,218, assigned to the assignee of the present case. The disclosure of the '218 patent is incorporated herein in its entirety.

Figure 29:
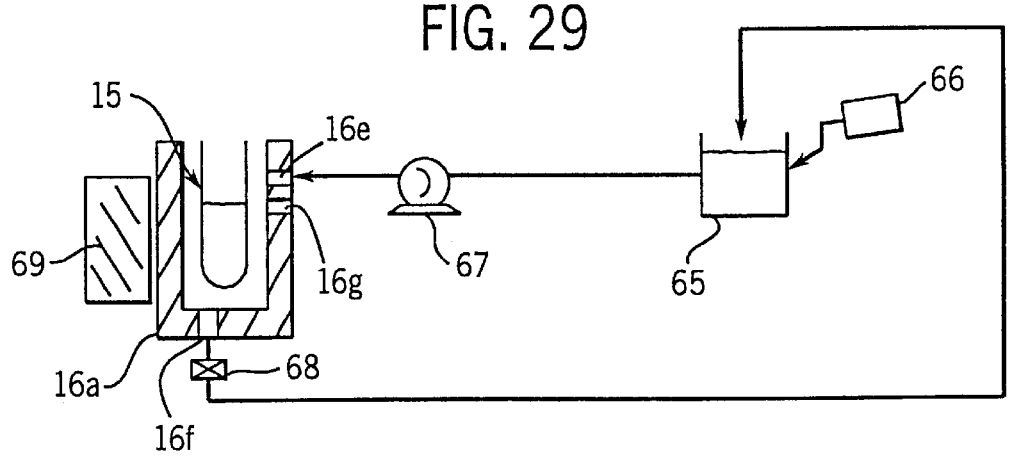
FIG. 29 is a generic view of operation of a portion of the structures described herein.

The module 16a shown in FIGS. 3A and 3B can provide thermal cycling of reaction contents in second container 15 with use of heated or chilled fluids as shown in FIG. 29. Fluid is stored reservoir 65 and heated or chilled by thermal controller 66. Fluid is routed to module 16a through port 16e at desired times by metering fan or pump 67. Heat transfer occurs between the contents in second container 15 and the heated or chilled fluid. The metered amount of fluid transferred to module 16a determines the time contents in second container 15 will remain at a given temperature. Evacuation of fluid from module 16a occurs through port 16f with use of valve 68 and/or additional pumps or gravity to container 65 or to waste. Given that thermal mass of second container 15, second container 15 contents and metered fluid contained in container 65 are known, the temperature of a metered fluid interaction with second container 15 may be calculated and predicted thereby reducing a need for temperature control at the interface of the fluid with the second container 15.

Different temperatures of contents in second container 15 can be achieved, e.g., by adding additional reservoir pumps and ports, such as port 16g shown in FIG. 29. To enhance performance of rapid heat transfer, second container 15 can be constructed as a pouch out of a thin polymeric film. Also, thermal element 69 may be positioned adjacent to and in contact with module 16a and controlled at a desired temperature.

Figure 28:
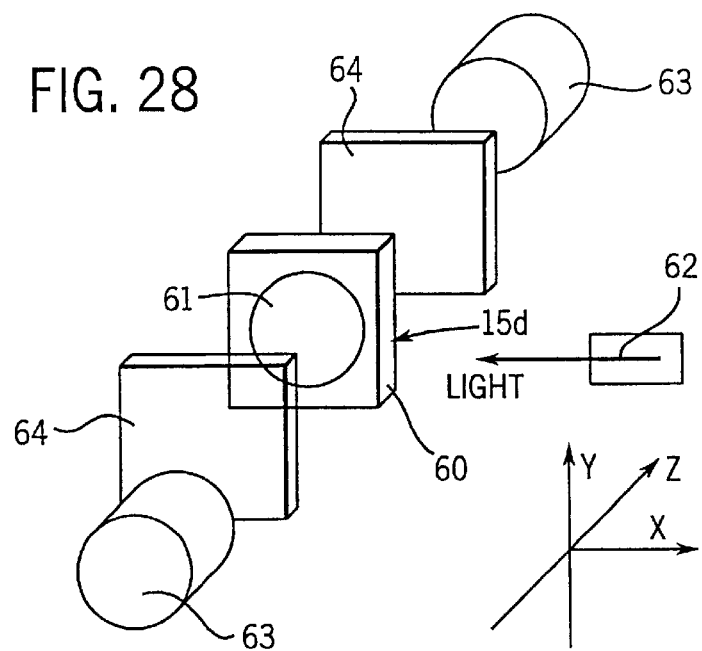
FIG. 28 is a perspective view of an optical configuration for use with the structures described herein.

Orientation of detector optics to second container 15 or 15d, for example, may be accomplished in many ways, one such way being shown in FIG. 28. Second container 15d may include at least one first face 60 on a first axis plane, designated 'YZ', and at least one second face 61 on a second axis plane 'XY'. An optical source 62 may be located adjacent to the first face 60 and an optical detector 63 may be located adjacent to a second face 61 opposite the first face 60 such that excitation of a label associated with an item of interest is induced by optical source 62 and emission of a signal, such as light, from the label is detected by detector or detector pair 63. The relative position of a first axis plane is different from the second axis plane to provide an increased signal collection area. The detector or detector pair 63 may be a single photodiode, quadrant photodiode, diode array, photomultiplier tube, or any combination of these detection devices. Combining optics with heating elements can be done with use of transparent heating elements 64 mounted in transparent material, such as glass, the heaters being located adjacent to at least one of the second faces of the second container 15d, and possibly lying on the second plane. In some embodiments, the optical source 62 may lie on a plane substantially orthogonal to the detector or detector pair 63. In this optical configuration, second container 15d could be a reaction tube supplied by Cepheid of Sunnyvale, Calif., or be any reaction container configuration including but not limited to a substantially hemispherical, spherical, cubic, or tetrahedron shape.

It is to be noted that additional first container 1 contents preparation, immunodiagnostic, and/or determination processing modules may be connected together with a common robotic and/or system processor, such as a computer and the like. It should also be noted that the heat transfer/detection apparatus 16 could accept first container 1 contents or other sample, processed or not, from another process path not operatively coupled to the structures 1a through 1i.

The described elements comprising the structures 1a through 1i may be selectively automatically and/or manually operated at desired times to accomplish a desired determination of an item of interest. The functions of the elements can be performed in any desired order any desired number of times to achieve desired results. The methods of operation and items, such as reagents and the like, used may be substantially similar to those described in U.S. Pat. No. 5,234,809, the disclosure of which is incorporated herein in its entirety.

The following example of a DNA/RNA sample extraction protocol and polymerase chain reaction (PCR) protocol illustrates such an application. The time periods, temperatures, volumes and elements (containers, solutions, reagents, etc.) used can be adjusted as desired. The position numbers correspond to the structure 1b of FIGS. 3A and 3B. However, the position numbers may also indicate the number of stepwise movements along a process path in the same manner as used to described the various assay formats in the '784 patent.

1 Tube DNA/RNA 20-20 Min Sample Preparation Protocol and 1 Tube 1.5 hr PCR End Point Protocol Sample Prep 0 Seconds—At Position 0:
  Instrument loads first container 1 onto first process path 11

1–36 Seconds—At Position 1:
  Pipettor 19 engages a disposable pipette tip 28, aspirates magnetically responsive microparticles (about 0.1 ml) from container 31 in reagent storage area 18, and dispenses those microparticles into first container 1 at Position 1. The disposable pipette tip 28 is washed with fluid in wash cup 23. Pipettor 19 aspirates another reagent (about 0.05 ml), such as an internal control and the like, from a container located in reagent handling area 13, dispenses that reagent into first container 1, and disposable pipette tip 28 is washed with fluid in wash cup 23 a second time. Sample (about 1 ml) disposed in container 8 is aspirated by pipettor 19 and dispensed into first container 1. Disposable pipette tip 28 is removed from pipettor 19 and deposited in tip waste 24. Alternately, the pipettor wash performed after microparticle dispense can be eliminated. In this case, microparticles and internal control are aspirated and dispensed into first container 1 substantially simultaneously or sequentially. Alternatively, a subset of or all liquid washes can be eliminated, in which case, microparticles, internal controls and sample may be aspirated and simultaneously and/or sequentially dispensed into first container 1.

37–72 Seconds—At Position 2:
  A dispense nozzle coupled to first process path 11 is fluidically connected to a reagent container, such as reagent bottle 32 as shown in FIGS. 5B and 19, containing a lyse solution. About 6 mL of lyse solution is dispensed, either at room temperature or at about 37 degrees Celsius, to the first container 1.

73–108 Seconds—At Position 3:
  Contents of first container 1 are mixed with mixer 5. First container 1 contents are incubated at about 37 degrees Celsius.

109–1260 Seconds—At Positions 4 through 35:
  Continue incubation for about 19.8 minutes at about 37 degrees Celsius. First container 1 contents are mixed at about 648 seconds and at about 1224 seconds. Periodic mixing of first container 1 contents enhances reaction.

1261–1296 Seconds—At Position 36:
  Item of interest bound to microparticles are captured on side wall of first container 1 with magnet 4.

1297–1332 Seconds—At Position 37:
  Elements comprising the wash zone 50 perform wash functions, described herein, comprising magnetic separation and aspiration and dispense of fluids with probe 49. Specifically, microparticles are separated from the remainder of first container 1 contents by magnet 4 and probe 49 removes the unseparated first container 1 contents. A wash solution (buffer) is dispensed from the probe 49 into the first container 1. Probe 49 is washed. Alternately, wash functions performed separately at, e.g. positions 36 and 37 can be combined at one position on first process path 11.

1333–1368 Seconds—At Position 38:
  Probe 49 performs wash and dispense functions. Mixer 5 provides resuspension of microparticles into fluid, specifically wash solution #1 in this example, in the first container 1. Alternately, resuspension of microparticles can be accomplished with appropriate fluid dispense into first container 1 as described above with respect to FIG. 17. Alternatively, functions performed at positions 36, 37, and/or 38 can be combined at one position on first process path 11.

1369–1404 Seconds—At Position 39:
  Item of interest bound to microparticles are captured on side wall of first container 1 with magnet 4. Elements comprising the wash zone 50 perform wash functions, described herein, comprising magnetic separation and aspiration and dispense of fluids with probe 49. Specifically, microparticles are separated from the remainder of first container 1 contents by magnet 4 and probe 49 removes the unseparated first container 1 contents. Probe 49 is washed. Alternately, wash functions performed separately at, e.g. positions 36 and 37 can be combined at one position on first process path 11.

1405–1440 Seconds—At Position 40:
  Probe 49 performs wash and dispense functions. Mixer 5 provides resuspension of microparticles into fluid in the first container 1. Alternately, resuspension of microparticles can be accomplished with appropriate fluid dispense into first container 1 as described above with respect to FIG. 17. Functions performed at positions 36, 37, and/or 38 can be combined at one position on first process path 11.

1441–1476 Seconds—At Position 41:
  Item of interest bound to microparticles are captured on side wall of first container 1 with magnet 4. Elements comprising the wash zone 50 perform wash functions, described herein, comprising magnetic separation and aspiration and dispense of fluids with probe 49. Specifically, microparticles are separated from the remainder of first container 1 contents by magnet 4 and probe 49 removes the unseparated first container 1 contents. A wash solution (buffer) is dispensed from the probe 49 into the first container 1. Probe 49 is washed. Alternately, wash functions performed separately at, e.g. positions 36 and 37 can be combined at one position on first process path 11.

1477–1512 Seconds—At Position 42:
  Probe 49 performs wash and dispense functions. Mixer provides resuspension of microparticles into fluid, specifically wash solution #2 in this example, in the first container 1. Alternately, resuspension of microparticles can be accomplished with appropriate fluid dispense into first container 1 as described above with respect to FIG. 17. Functions performed at positions 36, 37, and/or 38 can be combined at one position on first process path 11.

1513–1548 Seconds— At Position 43:
  Item of interest bound to microparticles are captured on side wall of first container 1 with magnet 4. Elements comprising the wash zone 50 perform wash functions, described herein, comprising magnetic separation and aspiration and dispense of fluids with probe 49. Specifically, microparticles are separated from the remainder of first container 1 contents by magnet 4 and probe 49 removes the unseparated first container 1 contents. A wash solution (buffer) is dispensed from the probe 49 into the first container 1. Probe 49 is washed. Alternately, wash functions performed separately at, e.g. positions 36 and 37 can be combined at one position on first process path 11.

1549–1584 Seconds—At Position 44:

Probe 49 performs wash and dispense functions. Mixer 5 provides resuspension of microparticles into fluid, specifically wash solution #2 in this example, in the first container 1. Alternately, resuspension of microparticles can be accomplished with appropriate fluid dispense into first container 1 as described above with respect to FIG. 17.

1584–1620 Seconds— At Position 45:

Item of interest bound to microparticles are captured on side wall of first container 1 with magnet 4. Elements comprising the wash zone 50 perform wash functions, described herein, comprising magnetic separation and aspiration and dispense of fluids with probe 49. Specifically, microparticles are separated from the remainder of first container 1 contents by magnet 4 and probe 49 removes the unseparated first container 1 contents. Probe 49 is washed. Alternately, wash functions performed separately at, e.g. positions 36 and 37 can be combined at one position on first process path 11.

Figure 5E:
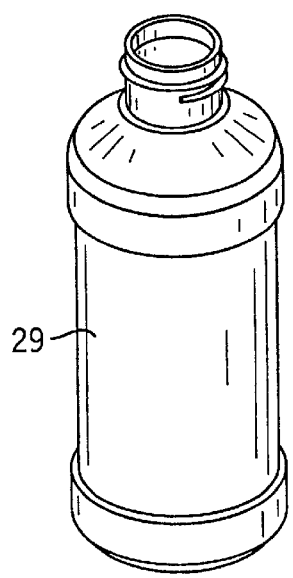
Figure 5F:
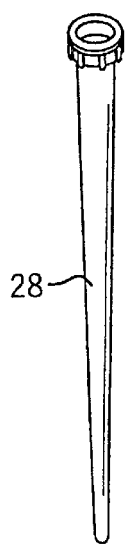

1621–1656 Seconds—At Position 46:

A pump, operatively associated with the first process path 11, connected fluidly with a dispense nozzle, and fluidly coupled with the first process path 11, and a reagent container, such as container 29 shown in FIGS. 5E and 19, induces dispense of a fluid, such as an elution reagent, to first container 1. In one embodiment, about 80 $\mu$L of elution reagent is dispensed at ambient temperature or, alternately, at about 70 degrees Celsius.

1657–2844 Seconds— At Positions 47–76:

First container 1 contents are incubated, for a period of about 19.8 minutes, in this example at about 37 degrees Celsius, or at a temperature substantially within the range of about 50 to about 70 degrees Celsius. Periodic mixing enhances reactions among elements of the first container 1 contents. Elution reagent releases the item of interest from the microparticles.

Assay

2845–2880 Seconds—At Position 77:

At position 76, pipettor 12 engages a disposable pipettor tip 28, aspirates a first reagent from a container in reagent storage area 13, and dispenses that reagent into second container 15 on container processor line 15a. The disposable pipette tip 28 is washed with fluid in wash cup 24. Pipettor 12 aspirates a second reagent from a container in reagent handling area 13, dispenses the second reagent into second container 15, and disposable pipette tip 28 is washed with in wash cup 24. A third reagent is aspirated into pipette tip 28 from a container in reagent handling area 13, and the first container 1 contents containing the item of interest, about 50 $\mu$L, is aspirated from first container 1 in position 77 of first process path 11 to the pipette tip 28. The third reagent and the aspirated first container 1 contents are dispensed from the pipette tip 28 into second container 15 and pipettor 12 ejects disposable pipette tip 28 to tip waste 24. Alternately, the third reagent can be dispensed into first container 1 on first process path 11 at position 76 by pipettor 12 or by another dispense nozzle on the first process path 11. In another embodiment, the first reagent and second reagent aspirations can be completed, without washing the pipettor 12 between aspirations, and the reagents can be dispensed into second container 15 substantially simultaneously. The volumes of each of the three reagents may be substantially within the range of about 10 to about 50 $\mu$L. If it were desired to detect more than one item of interest in a given sample, portions of the contents of first container 1 can be transferred to a corresponding number of containers 15. These multiple transfers of first container 1 contents may occur from position 77 or, alternately, may occur from position 77 and subsequent position(s). If a relatively large number, such as about 15, of items of interest are to be determined from one sample, then multiple aspirations and dispenses can occur from container 8 and/or first container 1 by pipettors 19 and/or 12.

2881–2916 Seconds

Second container 15 is transported on the container processor line 15a to the sealer 21 where the second container 15 is sealed. The sealed second container 15 is transported to the spinner 22 where the contents in the upper portion of second container 15 are moved to the lower portion of second container 15.

2917–2952 Seconds

A robot engages second container 15, and places the second container 15 in a heat transfer/detection module 16a where the second container 15 is exposed to a thermal cycle and the item of interest in the second container 15 is detected.

2953–8352 Seconds—

Assay Specific Thermal Cycling Protocols:

Second container 15 undergoes a thermal cycling protocol as specified. The following are a few examples of such a protocol.

Protocol A 1. about 59 degrees Celsius for about 30 minutes. One cycle
2. about 95 degrees Celsius for about 30 seconds, about 54 degrees Celsius for about 30 seconds, about 72 degrees Celsius for about 30 seconds. 4 cycles
3. about 90 degrees Celsius for about 30 seconds, about 59 degrees Celsius for about 30 seconds, about 72 degrees Celsius for about 30 seconds. 46 cycles
4. about 94 degrees Celsius for about 5 minutes, about 45 degrees Celsius for about 15 minutes, about 25 degrees Celsius for about 10 min. 1 cycle Protocol B 1. about 94 degrees Celsius for about 10 minutes. One cycle.
2. about 94 degrees Celsius for about 1 minute, about 58 degrees Celsius for about 1 minute. 45 cycles.
3. about 58 degrees Celsius for about 10 minutes, about 94 degrees Celsius for about 5 minutes, about 55 degrees Celsius for about 15 minutes, about 25 degrees Celsius and maintain.

Protocol C 1. about 95 degrees Celsius for about 9.5 minutes. One cycle.
2. about 95 degrees Celsius for about 30 seconds, about 59 degrees Celsius for about 1 minute. 41 cycles.

3. about 95 degrees Celsius for about 3 minutes, about 25 degrees Celsius for about 10 minutes. One cycle 8353–8388 Seconds After completion of the particular thermal cycling protocol selected, the item of interest in the second container 15 is detected and the second container 15 is disposed. A result of the above steps is reported.

In any of the embodiments described herein, lysis may include use of induced electrical pulse(s) or sonication whereby such pulsing causes DNA/RNA to be exposed in undamaged form prior to binding.

In addition to the above-disclosed DNA/RNA method or protocol, the method performed by the structures 1a through 1g may be an immunodiagnostic method. For example, U.S. Pat. No. 5,795,784 lists various methods or formats that may be executed with the above-disclosed structures 1a through 1g, possibly with appropriate modification. Furthermore, DNA/RNA extraction could be amplified and detected with the structures 1a through 1g, or alternately transported to another structure 1a or a different structure, such as those disclosed in the '784 patent and the like, for further processing. It is understood that first container 1 could be sealed by suitable means, if desired.

In another embodiment, the contents of first container 1, after processing discussed above, can be transferred from Position 76 on the first process path 11 to an optical flow cell on the structure. The optical flow cell is substantially similar to that described in the following U.S. Pat. Nos. 5,589,394, 5,601,234, 5,631,165, 5,631,730, 5,656,499, 5,812,419, and 5,891,734. Those patents are assigned to the assignee of the present case and the disclosures thereof are incorporated herein in their entirety. The item of interest in the sample can be detected with the optical flow cell.

In a modification of this embodiment, sample directly from first container 1, 8, 15, or another sample carrying vessel can be transferred to a sample receiving cups on the structure. The sample can be mixed and suitably incubated with a reagent containing a label. The reagent may be formulated such that the label encounters or passes through cell and/or nuclear membranes in the sample thereby permitting the label to bind or otherwise to become associated with the item of interest in the sample irrespective of where the item of interest is located within the sample. If the label encounters no item of interest in the sample, such as if no item of interest is present in the sample or if all items of interest in the sample are already associated with a label, then the label or excess label can be removed by suitable methods, such as separation, washing, etc. The sample, possibly containing an item of interest associated with a label, is passed to the optical flow cell on the structure and the label is detected by optics associated with the flow cell thereby indicating presence of the item of interest.

What is claimed is:

1. A method of performing a determination of an item of interest in a sample using a single structure having a first process path and a second process path, and the second process path includes a plurality of second process sub-paths, the method comprising the steps of:
   (a) providing a sample accessible to the single structure;
   (b) placing a first container for processing the sample in a first process path on the single structure;
   (c) transferring the sample to the first container in the first process path;
   (d) adding a reagent to the first container in the first process path;
   (e) mixing contents of the first container in the first process path;
   (f) separating the item of interest in the sample from the contents of the first container in the first process path;
   (g) transferring the separated item of interest in the sample from the first container in the first process path to a second container in at least one of the plurality of second process sub-paths of the second process path on the single structure;
   (h) bringing contents of the second container to a first temperature different from a temperature of the first process path in the second path; and
   (i) detecting the item of interest in the second container in the second process path.

2. A method as defined in claim 1 further comprising the step of:
   (j) transferring a second sample to a second first container in the first process path;
   (k) adding a reagent to the second first container in the first process path; and
   (l) detecting the item of interest in the second first container in the first process path.

3. A method as defined in claim 1 further comprising the step of:
   (j) sealing at least one of the first container and the second container.

4. A method as defined in claim 3 further comprising the step of:
   (k) removing the seal from at least one of the first container and the second container.

5. A method as defined in claim 1 further comprising the step of:
   (j) reducing exposure of contents of at least one of the first container and the second container to a contaminant.

6. A method as defined in claim 1 further comprising the step of:
   (j) bringing contents of the second container to a second temperature different from the first temperature in the second process path.

7. A method as defined in claim 1 further comprising the steps of:
   (j) transferring a second sample to a second first container in the first process path;
   (k) adding a reagent to the second first container in the first process path;
   (l) transferring contents of the second first container to an optical flow cell on the single structure;
   (m) illuminating the optical flow cell; and
   (n) detecting the item of interest in the sample in the optical flow cell.

8. A method as defined in claim 1 wherein a determination of an item of interest comprises at least one process, the method further comprising the steps of:
   (j) discerning determinations to be performed by the single structure;
   (k) sorting samples provided to the single structure by at least one common process; and
   (l) transferring the samples to the first process path in an order determined by sorting step (k).

9. A method as defined in claim 8 further comprising the step of:
   (m) allocating an element of the single structure to a given determination based on sorting step (k).

10. A method as defined in claim 1 wherein the sample is maintained at more than one temperature in the first process path.

11. A method as defined in claim 10 wherein the first process path includes more than one temperature controller.

* * * * *